United States Patent
Alexander et al.

(10) Patent No.: US 12,090,290 B2
(45) Date of Patent: Sep. 17, 2024

(54) SHAPE MEMORY ACTUATORS FOR ADJUSTABLE SHUNTING SYSTEMS, AND ASSOCIATED SYSTEMS AND METHODS

(71) Applicant: Shifamed Holdings, LLC, Campbell, CA (US)

(72) Inventors: Miles Alexander, Fremont, CA (US); Scott Robertson, Portland, OR (US); Peter Andriola, Castro Valley, CA (US); Brian Fahey, Menlo Park, CA (US); Matthew Lane Pease, Mountain View, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 17/797,626

(22) PCT Filed: Mar. 8, 2022

(86) PCT No.: PCT/US2022/019374
§ 371 (c)(1),
(2) Date: Aug. 4, 2022

(87) PCT Pub. No.: WO2022/192280
PCT Pub. Date: Sep. 15, 2022

(65) Prior Publication Data
US 2023/0201545 A1    Jun. 29, 2023

Related U.S. Application Data

(60) Provisional application No. 63/158,508, filed on Mar. 9, 2021.

(51) Int. Cl.
*A61M 27/00* (2006.01)
*A61B 17/11* (2006.01)

(52) U.S. Cl.
CPC .... *A61M 27/002* (2013.01); *A61B 2017/1139* (2013.01)

(58) Field of Classification Search
CPC ........ A61M 27/002; A61M 2205/0266; A61M 2025/0233; A61M 2205/3653;
(Continued)

(56) References Cited

U.S. PATENT DOCUMENTS 3,874,388 A    4/1975  King et al.
4,601,309 A    7/1986  Chang
(Continued)

FOREIGN PATENT DOCUMENTS

AU    2005211243    8/2005
AU    2010344182    8/2012
(Continued)

OTHER PUBLICATIONS http://www.collinsdictionary.com/dictionary/english/actuator. Accessed Oct. 18, 2023.*

(Continued)

*Primary Examiner* — Adam Marcetich
(74) *Attorney, Agent, or Firm* — Perkins Coie LLP

(57) ABSTRACT

The present technology is directed to adjustable shunting systems having a shunting element, a shape memory actuator, and a lumen extending therethrough for transporting fluid. The shape memory actuator can have a plurality of struts proximate the shunting element and a plurality of projections extending from the plurality of struts. In operation, the shape memory actuator can be used to adjust a geometry of the lumen. In some embodiments, the system is configured such that (a) any strain in the shape memory actuator is concentrated in the struts, and/or (b) the struts experience greater resistive heating than the projections when an electrical current is applied to the actuator.

18 Claims, 10 Drawing Sheets

(58) Field of Classification Search
CPC ......... A61M 25/04; A61B 2017/00575; A61B 2017/00592; A61B 17/0057; A61B 2017/00867; A61B 17/12168; A61B 2017/00084; A61B 2017/00862; A61B 2017/1139; A61B 2017/12054; A61B 2018/1435; A61F 2210/0033; A61F 2/24; A61F 2/2418; A61F 2210/0014; A61F 2/82; A61F 2/95

See application file for complete search history.

(56) References Cited

U.S. PATENT DOCUMENTS

| | | | |
|---|---|---|---|
| 4,662,355 | A | 5/1987 | Pieronne et al. |
| 4,705,507 | A | 11/1987 | Boyles |
| 4,836,204 | A | 6/1989 | Landymore et al. |
| 4,979,955 | A | 12/1990 | Smith |
| 4,995,857 | A | 2/1991 | Arnold |
| 5,186,431 | A | 2/1993 | Tamari |
| 5,197,978 | A | 3/1993 | Hess |
| 5,267,940 | A | 12/1993 | Moulder |
| 5,290,227 | A | 3/1994 | Pasque |
| 5,312,341 | A | 5/1994 | Turi |
| 5,326,374 | A | 7/1994 | Ilbawi et al. |
| 5,332,402 | A | 7/1994 | Teitelbaum |
| 5,334,217 | A | 8/1994 | Das |
| 5,409,019 | A | 4/1995 | Wilk |
| 5,429,144 | A | 7/1995 | Wilk |
| 5,500,015 | A | 3/1996 | Deac |
| 5,531,759 | A | 7/1996 | Kensey et al. |
| 5,556,386 | A | 9/1996 | Todd |
| 5,584,803 | A | 12/1996 | Stevens et al. |
| 5,597,377 | A | 1/1997 | Aldea |
| 5,611,338 | A | 3/1997 | Gallup |
| 5,645,559 | A | 7/1997 | Hachtman et al. |
| 5,655,548 | A | 8/1997 | Nelson et al. |
| 5,662,711 | A | 9/1997 | Douglas |
| 5,702,412 | A | 12/1997 | Popov et al. |
| 5,725,552 | A | 3/1998 | Kotula et al. |
| 5,741,297 | A | 4/1998 | Simon |
| 5,795,307 | A | 8/1998 | Krueger |
| 5,810,836 | A | 9/1998 | Hussein et al. |
| 5,824,071 | A | 10/1998 | Nelson et al. |
| 5,916,193 | A | 6/1999 | Stevens et al. |
| 5,941,850 | A | 8/1999 | Shah et al. |
| 5,944,019 | A | 8/1999 | Kundson et al. |
| 5,957,949 | A | 9/1999 | Leonhardt et al. |
| 6,039,759 | A | 3/2000 | Carpentier et al. |
| 6,077,298 | A | 6/2000 | Tu et al. |
| 6,120,534 | A | 9/2000 | Ruiz |
| 6,126,686 | A | 10/2000 | Badylak et al. |
| 6,165,188 | A | 12/2000 | Saadat et al. |
| 6,165,209 | A | 12/2000 | Patterson et al. |
| 6,210,318 | B1 | 4/2001 | Lederman |
| 6,217,541 | B1 | 4/2001 | Yu |
| 6,240,322 | B1 | 5/2001 | Peterfeso et al. |
| 6,242,762 | B1 | 6/2001 | Brown et al. |
| 6,254,564 | B1 | 7/2001 | Wilk et al. |
| 6,260,552 | B1 | 7/2001 | Mortier et al. |
| 6,270,526 | B1 | 8/2001 | Cox |
| 6,277,078 | B1 | 8/2001 | Porat et al. |
| 6,302,892 | B1 | 10/2001 | Wilk |
| 6,328,699 | B1 | 12/2001 | Eigler et al. |
| 6,344,022 | B1 | 2/2002 | Jarvik |
| 6,358,277 | B1 | 3/2002 | Duran |
| 6,406,422 | B1 | 6/2002 | Landesberg |
| 6,447,539 | B1 | 9/2002 | Nelson et al. |
| 6,451,051 | B2 | 9/2002 | Drasler et al. |
| 6,458,153 | B1 | 10/2002 | Bailey et al. |
| 6,468,303 | B1 | 10/2002 | Amplatz et al. |
| 6,478,776 | B1 | 11/2002 | Rosenman et al. |
| 6,491,705 | B2 | 12/2002 | Gifford, III et al. |
| 6,514,285 | B1 * | 2/2003 | Pinchasik ................ B21F 3/04 623/1.22 |
| 6,527,698 | B1 | 3/2003 | Kung et al. |
| 6,544,208 | B2 | 4/2003 | Ethier et al. |
| 6,562,066 | B1 | 5/2003 | Martin |
| 6,572,652 | B2 | 6/2003 | Shaknovich |
| 6,589,198 | B1 | 7/2003 | Soltanpour et al. |
| 6,632,169 | B2 | 10/2003 | Korakianitis et al. |
| 6,638,303 | B1 | 10/2003 | Campbell |
| 6,641,610 | B2 | 11/2003 | Wolf et al. |
| 6,652,578 | B2 | 11/2003 | Bailey et al. |
| 6,685,664 | B2 | 2/2004 | Levin et al. |
| 6,712,836 | B1 | 3/2004 | Berg et al. |
| 6,783,499 | B2 | 8/2004 | Schwartz |
| 6,909,920 | B2 | 6/2005 | Lokhoff et al. |
| 6,911,043 | B2 | 6/2005 | Myers et al. |
| 6,926,670 | B2 | 8/2005 | Rich et al. |
| 7,001,409 | B2 | 2/2006 | Amplatz |
| 7,011,095 | B2 | 3/2006 | Wolf et al. |
| 7,056,294 | B2 | 6/2006 | Khairkhahan et al. |
| 7,149,587 | B2 | 12/2006 | Wardle et al. |
| 7,175,656 | B2 | 2/2007 | Khairkhahan |
| 7,270,675 | B2 | 9/2007 | Chun et al. |
| 7,294,115 | B1 | 11/2007 | Wilk |
| 7,311,690 | B2 | 12/2007 | Burnett |
| 7,311,730 | B2 | 12/2007 | Gabbay |
| 7,317,951 | B2 | 1/2008 | Schneider et al. |
| 7,389,134 | B1 | 6/2008 | Karicherla et al. |
| 7,390,310 | B2 | 6/2008 | McCusker et al. |
| 7,513,908 | B2 | 4/2009 | Lattouf |
| 7,524,329 | B2 | 4/2009 | Rucker |
| 7,524,330 | B2 | 4/2009 | Berreklouw |
| 7,524,332 | B2 | 4/2009 | Osborne et al. |
| 7,608,067 | B2 | 10/2009 | Bonni |
| 7,615,010 | B1 | 11/2009 | Najafi et al. |
| 7,617,001 | B2 | 11/2009 | Penner et al. |
| 7,634,318 | B2 | 12/2009 | Tran et al. |
| 7,658,747 | B2 | 2/2010 | Forde et al. |
| 7,699,059 | B2 | 4/2010 | Fonseca et al. |
| 7,736,327 | B2 | 6/2010 | Wilk et al. |
| 7,780,725 | B2 | 8/2010 | Haug et al. |
| 7,794,473 | B2 | 9/2010 | Tessmer et al. |
| 7,806,921 | B2 | 10/2010 | Hoffman |
| 7,860,579 | B2 | 12/2010 | Goetzinger et al. |
| 7,892,246 | B2 | 2/2011 | Akin et al. |
| 7,905,901 | B2 | 3/2011 | Corcoran et al. |
| 7,922,764 | B2 | 4/2011 | Gordy et al. |
| 7,938,840 | B2 | 5/2011 | Golden et al. |
| 7,967,769 | B2 | 6/2011 | Faul et al. |
| 7,988,724 | B2 | 8/2011 | Salahieh et al. |
| 8,012,198 | B2 | 9/2011 | Hill et al. |
| 8,016,877 | B2 | 9/2011 | Seguin et al. |
| 8,043,360 | B2 | 10/2011 | McNamara et al. |
| 8,070,708 | B2 | 12/2011 | Rottenberg et al. |
| 8,091,556 | B2 | 1/2012 | Keren et al. |
| 8,096,959 | B2 | 1/2012 | Stewart et al. |
| 8,147,545 | B2 | 4/2012 | Avior |
| 8,157,860 | B2 | 4/2012 | McNamara et al. |
| 8,172,896 | B2 | 5/2012 | McNamara et al. |
| 8,235,916 | B2 | 8/2012 | Whiting et al. |
| 8,235,933 | B2 | 8/2012 | Keren et al. |
| 8,246,677 | B2 | 8/2012 | Ryan |
| 8,252,042 | B2 | 8/2012 | McNamara et al. |
| 8,303,511 | B2 | 11/2012 | Eigler et al. |
| 8,328,751 | B2 | 12/2012 | Keren et al. |
| 8,348,996 | B2 | 1/2013 | Tuval et al. |
| 8,398,708 | B2 | 3/2013 | Meiri et al. |
| 8,460,366 | B2 | 6/2013 | Rowe |
| 8,460,372 | B2 | 6/2013 | McNamara et al. |
| 8,597,225 | B2 | 12/2013 | Kapadia |
| 8,647,381 | B2 | 2/2014 | Essinger et al. |
| 8,696,611 | B2 | 4/2014 | Nitzan et al. |
| 8,740,962 | B2 | 6/2014 | Finch et al. |
| 8,745,845 | B2 | 6/2014 | Finch et al. |
| 8,747,458 | B2 | 6/2014 | Tuval et al. |
| 8,752,258 | B2 | 6/2014 | Finch et al. |
| 8,764,848 | B2 | 7/2014 | Callaghan et al. |
| 8,882,697 | B2 | 11/2014 | Celermajer et al. |
| 8,951,223 | B2 | 2/2015 | McNamara et al. |
| 9,005,155 | B2 | 4/2015 | Sugimoto |
| 9,034,034 | B2 | 5/2015 | Nitzan et al. |
| 9,138,213 | B2 | 9/2015 | Amin et al. |

(56) References Cited

U.S. PATENT DOCUMENTS

| | | |
|---|---|---|
| 9,180,005 B1 | 11/2015 | Lashinski et al. |
| 9,204,842 B2 | 12/2015 | Mothilal et al. |
| 9,205,236 B2 | 12/2015 | McNamara et al. |
| 9,232,997 B2 | 1/2016 | Sugimoto et al. |
| 9,277,995 B2 | 3/2016 | Celermajer et al. |
| 9,358,371 B2 | 6/2016 | McNamara et al. |
| 9,456,812 B2 | 10/2016 | Finch et al. |
| 9,610,041 B2 | 4/2017 | Foster et al. |
| 9,629,715 B2 | 4/2017 | Nitzan et al. |
| 9,642,993 B2 | 5/2017 | McNamara et al. |
| 9,649,480 B2 | 5/2017 | Sugimoto et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,775,636 B2 | 10/2017 | Fazio et al. |
| 9,918,856 B2 | 3/2018 | Favier et al. |
| 9,937,036 B2 | 4/2018 | Sugimoto et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,076,403 B1 | 9/2018 | Eigler et al. |
| 10,188,375 B2 | 1/2019 | McNamara et al. |
| 10,207,087 B2 | 2/2019 | Keren |
| 10,251,740 B2 | 4/2019 | Eigler et al. |
| 10,292,690 B2 | 5/2019 | Celermajer et al. |
| 10,350,384 B2 | 7/2019 | Farnan et al. |
| 10,357,357 B2 | 7/2019 | Levi et al. |
| 10,368,981 B2 | 8/2019 | Nitzan et al. |
| 10,376,359 B2 | 8/2019 | Essinger et al. |
| 10,376,680 B2 | 8/2019 | McNamara et al. |
| 10,398,421 B2 | 9/2019 | Celermajer |
| 10,405,903 B1 | 9/2019 | Biesinger et al. |
| 10,413,284 B2 | 9/2019 | McNamara et al. |
| 10,413,286 B2 | 9/2019 | McNamara et al. |
| 10,463,477 B2 | 11/2019 | Forcucci et al. |
| 10,463,490 B2 | 11/2019 | Rottenberg et al. |
| 10,471,251 B1 | 11/2019 | Manicka |
| 10,478,594 B2 | 11/2019 | Yacoby et al. |
| 10,568,751 B2 | 2/2020 | McNamara |
| 10,588,611 B2 | 3/2020 | Magnin et al. |
| 10,610,210 B2 | 4/2020 | Finch et al. |
| 10,624,621 B2 | 4/2020 | Celermajer |
| 10,632,292 B2 | 4/2020 | Forcucci et al. |
| 10,639,459 B2 | 5/2020 | Nitzan et al. |
| 10,667,896 B2 | 6/2020 | Delaney, Jr. et al. |
| 10,675,450 B2 | 6/2020 | Finch |
| 10,828,151 B2 | 11/2020 | Nitzan et al. |
| 10,835,394 B2 | 11/2020 | Nae et al. |
| 10,898,698 B1* | 1/2021 | Eigler ............... A61B 17/0057 |
| 10,912,645 B2 | 2/2021 | Rottenberg et al. |
| 10,925,706 B2 | 2/2021 | Eigler et al. |
| 10,932,786 B2 | 3/2021 | McNamara et al. |
| 10,940,296 B2 | 3/2021 | Keren |
| 10,945,716 B2 | 3/2021 | Chen et al. |
| 11,135,410 B2 | 10/2021 | Finch et al. |
| 11,253,685 B2 | 2/2022 | Fahey et al. |
| 11,622,695 B1 | 4/2023 | Andriola et al. |
| 11,633,194 B2 | 4/2023 | Alexander et al. |
| 11,801,369 B2 | 10/2023 | Fahey et al. |
| 11,857,197 B2 | 1/2024 | Alexander et al. |
| 2002/0072656 A1 | 6/2002 | Vantassel et al. |
| 2002/0142119 A1* | 10/2002 | Seward ............... A61L 29/126 428/371 |
| 2002/0161427 A1 | 10/2002 | Rabkin et al. |
| 2002/0169371 A1 | 11/2002 | Gilderdale |
| 2002/0169475 A1 | 11/2002 | Gainor et al. |
| 2002/0177891 A1 | 11/2002 | Miles et al. |
| 2003/0125798 A1 | 7/2003 | Martin |
| 2003/0127090 A1 | 7/2003 | Gifford et al. |
| 2003/0163190 A1 | 8/2003 | LaFont et al. |
| 2004/0016514 A1 | 1/2004 | Nien |
| 2004/0077988 A1 | 4/2004 | Tweden et al. |
| 2004/0088045 A1 | 5/2004 | Cox |
| 2004/0093075 A1 | 5/2004 | Kuehne |
| 2004/0143294 A1 | 7/2004 | Corcoran et al. |
| 2004/0147869 A1 | 7/2004 | Wolf et al. |
| 2004/0158143 A1 | 8/2004 | Flaherty et al. |
| 2004/0162514 A1 | 8/2004 | Alferness et al. |
| 2004/0186566 A1 | 9/2004 | Hindrichs et al. |
| 2004/0210190 A1 | 10/2004 | Kohler et al. |
| 2004/0215067 A1 | 10/2004 | Stiger et al. |
| 2004/0215323 A1 | 10/2004 | Stiger |
| 2005/0004641 A1 | 1/2005 | Pappu |
| 2005/0033351 A1 | 2/2005 | Newton |
| 2005/0060030 A1 | 3/2005 | Lashinski et al. |
| 2005/0101946 A1 | 5/2005 | Govari et al. |
| 2005/0148925 A1 | 7/2005 | Rottenberg et al. |
| 2005/0159789 A1 | 7/2005 | Brockway et al. |
| 2005/0165344 A1 | 7/2005 | Dobak, III |
| 2005/0192627 A1 | 9/2005 | Whisenant et al. |
| 2005/0204811 A1 | 9/2005 | Neff |
| 2005/0251212 A1* | 11/2005 | Kieval ............... A61N 1/36117 607/2 |
| 2005/0288722 A1 | 12/2005 | Eigler et al. |
| 2006/0009810 A1 | 1/2006 | Mann et al. |
| 2006/0025857 A1 | 2/2006 | Bergheim et al. |
| 2006/0047205 A1 | 3/2006 | Ludomirsky et al. |
| 2006/0064135 A1 | 3/2006 | Brockway |
| 2006/0111660 A1 | 5/2006 | Wolf et al. |
| 2006/0116625 A1 | 6/2006 | Renati et al. |
| 2006/0200030 A1 | 9/2006 | White et al. |
| 2007/0010837 A1 | 1/2007 | Tanaka |
| 2007/0010852 A1 | 1/2007 | Blaeser et al. |
| 2007/0043435 A1 | 2/2007 | Seguin et al. |
| 2007/0088220 A1 | 4/2007 | Stahmann |
| 2007/0088223 A1 | 4/2007 | Mann et al. |
| 2007/0112344 A1* | 5/2007 | Keilman ............ A61B 5/0031 606/41 |
| 2007/0118039 A1 | 5/2007 | Bodecker et al. |
| 2007/0150019 A1 | 6/2007 | Youker et al. |
| 2007/0213813 A1 | 9/2007 | Von Segesser et al. |
| 2007/0282157 A1 | 12/2007 | Rottenberg et al. |
| 2008/0033527 A1 | 2/2008 | Nunez et al. |
| 2008/0097276 A1 | 4/2008 | Bertrand et al. |
| 2008/0108904 A1 | 5/2008 | Heil |
| 2008/0119891 A1 | 5/2008 | Miles et al. |
| 2008/0127689 A1 | 6/2008 | McCusker et al. |
| 2008/0171941 A1 | 7/2008 | Huelskamp et al. |
| 2008/0208083 A1 | 8/2008 | Lin et al. |
| 2008/0208286 A1* | 8/2008 | Kieval ............... A61N 1/36071 607/46 |
| 2009/0025459 A1 | 1/2009 | Zhang et al. |
| 2009/0036975 A1 | 2/2009 | Ward et al. |
| 2009/0243956 A1 | 10/2009 | Keilman et al. |
| 2009/0270742 A1 | 10/2009 | Wolinsky et al. |
| 2009/0276040 A1 | 11/2009 | Rowe et al. |
| 2009/0281597 A1 | 11/2009 | Parramon et al. |
| 2010/0063375 A1 | 3/2010 | Kassab et al. |
| 2010/0076366 A1 | 3/2010 | Henderson, Sr. et al. |
| 2010/0076517 A1 | 3/2010 | Imran |
| 2010/0106028 A1 | 4/2010 | Penner et al. |
| 2010/0168672 A1 | 7/2010 | Carr |
| 2010/0179449 A1 | 7/2010 | Chow et al. |
| 2010/0241241 A1 | 9/2010 | McKnight et al. |
| 2010/0249560 A1 | 9/2010 | Levinson et al. |
| 2010/0262021 A1 | 10/2010 | Yadav et al. |
| 2010/0262036 A1 | 10/2010 | Najafi et al. |
| 2010/0275592 A1 | 11/2010 | Topliss et al. |
| 2010/0298930 A1 | 11/2010 | Orlov |
| 2011/0054515 A1 | 3/2011 | Bridgeman et al. |
| 2011/0082377 A1 | 4/2011 | Mahajan et al. |
| 2011/0218480 A1 | 9/2011 | Rottenberg et al. |
| 2011/0218481 A1 | 9/2011 | Rottenberg et al. |
| 2011/0257723 A1 | 10/2011 | McNamara |
| 2011/0264194 A1 | 10/2011 | Griswold |
| 2011/0282217 A1 | 11/2011 | Nashet |
| 2011/0295183 A1 | 12/2011 | Finch et al. |
| 2012/0053686 A1* | 3/2012 | McNamara ........ A61B 17/0057 623/2.36 |
| 2012/0059431 A1 | 3/2012 | Williams et al. |
| 2012/0197392 A1 | 8/2012 | DuMoutelle et al. |
| 2012/0215303 A1 | 8/2012 | Quadri et al. |

(56) References Cited

U.S. PATENT DOCUMENTS

| | | |
|---|---|---|
| 2012/0229272 A1 | 9/2012 | Jacob et al. |
| 2012/0265296 A1 | 10/2012 | McNamara et al. |
| 2012/0283773 A1 | 11/2012 | Van Tassel et al. |
| 2012/0290062 A1 | 11/2012 | McNamara et al. |
| 2013/0085350 A1 | 4/2013 | Schugt et al. |
| 2013/0123569 A1 | 5/2013 | Gross |
| 2013/0144379 A1 | 6/2013 | Najafi et al. |
| 2013/0178783 A1 | 7/2013 | Mcnamara et al. |
| 2013/0178784 A1 | 7/2013 | McNamara et al. |
| 2013/0190799 A1 | 7/2013 | Clark |
| 2013/0192611 A1 | 8/2013 | Taepke, II et al. |
| 2013/0197423 A1 | 8/2013 | Keren et al. |
| 2013/0211221 A1 | 8/2013 | Sunnarborg et al. |
| 2013/0253343 A1 | 9/2013 | Waldhauser et al. |
| 2013/0261531 A1 | 10/2013 | Gallagher et al. |
| 2013/0293025 A1 | 11/2013 | Xu et al. |
| 2014/0012342 A1 | 1/2014 | Penner et al. |
| 2014/0046427 A1 | 2/2014 | Michalak |
| 2014/0121750 A1* | 5/2014 | Hadley ............... A61F 2/848 |
| | | 623/1.36 |
| 2014/0128795 A1 | 5/2014 | Karen et al. |
| 2014/0128796 A1 | 5/2014 | Keren et al. |
| 2014/0135647 A1 | 5/2014 | Wolf, II |
| 2014/0163449 A1 | 6/2014 | Rottenberg et al. |
| 2014/0213915 A1 | 7/2014 | Doan et al. |
| 2014/0213916 A1 | 7/2014 | Doan et al. |
| 2014/0213959 A1 | 7/2014 | Nitzan et al. |
| 2014/0222040 A1 | 8/2014 | Park et al. |
| 2014/0222144 A1* | 8/2014 | Eberhardt ............ A61F 2/2418 |
| | | 623/2.38 |
| 2014/0249616 A1 | 9/2014 | Strauss et al. |
| 2014/0277054 A1 | 9/2014 | McNamara et al. |
| 2014/0306807 A1 | 10/2014 | Rowland et al. |
| 2015/0034217 A1 | 2/2015 | Vad |
| 2015/0039084 A1* | 2/2015 | Levi ................. A61F 2/2409 |
| | | 623/2.38 |
| 2015/0084585 A1 | 3/2015 | Moran |
| 2015/0119796 A1 | 4/2015 | Finch |
| 2015/0141807 A1 | 5/2015 | Fetterly |
| 2015/0148731 A1 | 5/2015 | Mcnamara et al. |
| 2015/0157268 A1 | 6/2015 | Winshtein et al. |
| 2015/0208929 A1 | 7/2015 | Rowland et al. |
| 2015/0223707 A1 | 8/2015 | Ludoph et al. |
| 2015/0230843 A1 | 8/2015 | Palmer et al. |
| 2015/0231387 A1 | 8/2015 | Harding et al. |
| 2015/0287544 A1 | 10/2015 | Irazoqui et al. |
| 2016/0022423 A1 | 1/2016 | Mcnamara et al. |
| 2016/0089079 A1 | 3/2016 | Stein |
| 2016/0151179 A1 | 6/2016 | Favier et al. |
| 2016/0158561 A1 | 6/2016 | Reddy |
| 2016/0235999 A1 | 8/2016 | Nuta et al. |
| 2016/0302808 A1* | 10/2016 | Loganathan ......... A61B 17/221 |
| 2016/0374682 A1 | 12/2016 | Leonard et al. |
| 2017/0014067 A1 | 1/2017 | Peppou et al. |
| 2017/0105635 A1 | 4/2017 | Cho et al. |
| 2017/0113026 A1 | 4/2017 | Finch |
| 2017/0312078 A1 | 11/2017 | Krivoruchko |
| 2017/0340460 A1 | 11/2017 | Rosen et al. |
| 2018/0014828 A1 | 1/2018 | Fonte et al. |
| 2018/0117341 A1 | 5/2018 | Kane et al. |
| 2018/0168463 A1 | 6/2018 | Morris et al. |
| 2018/0250014 A1 | 9/2018 | Melanson et al. |
| 2018/0256865 A1 | 9/2018 | Finch et al. |
| 2018/0262037 A1 | 9/2018 | Meskeus |
| 2018/0296375 A1* | 10/2018 | Van Langenhove ...... A61F 2/06 |
| 2018/0310839 A1 | 11/2018 | McCaffrey et al. |
| 2019/0000327 A1 | 1/2019 | Doan |
| 2019/0014993 A1 | 1/2019 | Kaiser |
| 2019/0015103 A1 | 1/2019 | Sharma |
| 2019/0021861 A1 | 1/2019 | Finch |
| 2019/0150758 A1 | 5/2019 | Sailey et al. |
| 2019/0167197 A1 | 6/2019 | Abuuassar et al. |
| 2019/0173505 A1 | 6/2019 | Koyama |
| 2019/0175883 A1 | 6/2019 | Wessler et al. |
| 2019/0192864 A1 | 6/2019 | Koop et al. |
| 2019/0254814 A1* | 8/2019 | Nitzan ................ A61F 2/2412 |
| 2019/0262118 A1* | 8/2019 | Eigler ..................... A61F 2/91 |
| 2019/0269392 A1 | 9/2019 | Celermajer et al. |
| 2019/0298556 A1 | 10/2019 | Bohn et al. |
| 2019/0307459 A1 | 10/2019 | Celermajer et al. |
| 2019/0328513 A1 | 10/2019 | Levi et al. |
| 2019/0336135 A1 | 11/2019 | Inouye et al. |
| 2019/0336163 A1 | 11/2019 | McNamara et al. |
| 2019/0350519 A1 | 11/2019 | Bailey et al. |
| 2020/0008870 A1 | 1/2020 | Gruba et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0085600 A1 | 3/2020 | Schwartz et al. |
| 2020/0188143 A1 | 6/2020 | McNamara |
| 2020/0196867 A1 | 6/2020 | Andersen et al. |
| 2020/0196876 A1 | 6/2020 | Minor et al. |
| 2020/0197178 A1 | 6/2020 | Vecchio |
| 2020/0229977 A1 | 7/2020 | Mixter et al. |
| 2020/0229981 A1 | 7/2020 | Mixter et al. |
| 2020/0229982 A1 | 7/2020 | Mixter et al. |
| 2020/0245991 A1 | 8/2020 | Celermajer |
| 2020/0253615 A1 | 8/2020 | Melanson et al. |
| 2020/0260991 A1 | 8/2020 | Rowlaud et al. |
| 2020/0261705 A1 | 8/2020 | Nitzan et al. |
| 2020/0268515 A1 | 8/2020 | Vettukattil et al. |
| 2020/0281611 A1* | 9/2020 | Kelly ................. A61B 17/221 |
| 2020/0315599 A1 | 10/2020 | Nae et al. |
| 2020/0368505 A1 | 11/2020 | Nae et al. |
| 2021/0030273 A1 | 2/2021 | Huang et al. |
| 2021/0038230 A1 | 2/2021 | Larsen et al. |
| 2021/0052378 A1 | 2/2021 | Nitzan et al. |
| 2021/0059527 A1 | 3/2021 | Najafi |
| 2021/0085935 A1 | 3/2021 | Fahey et al. |
| 2021/0100513 A1 | 4/2021 | Sahmauyar et al. |
| 2021/0100665 A1 | 4/2021 | Nae et al. |
| 2021/0121179 A1 | 4/2021 | Ben-david et al. |
| 2021/0145331 A1 | 5/2021 | Simpson et al. |
| 2021/0153776 A1 | 5/2021 | Minar et al. |
| 2021/0177508 A1 | 6/2021 | Kellerman |
| 2021/0205590 A1 | 7/2021 | Fahey et al. |
| 2021/0212638 A1 | 7/2021 | Golda et al. |
| 2021/0259732 A1 | 8/2021 | Dicicco et al. |
| 2021/0259829 A1 | 8/2021 | Quinn |
| 2021/0259839 A1 | 8/2021 | Cole et al. |
| 2021/0290214 A1 | 9/2021 | Cole et al. |
| 2021/0290356 A1 | 9/2021 | Srinkmann et al. |
| 2021/0298763 A1 | 9/2021 | Stahmann et al. |
| 2021/0299425 A1 | 9/2021 | Kume et al. |
| 2021/0299430 A1 | 9/2021 | Ratz et al. |
| 2021/0361238 A1 | 11/2021 | Bak-Boychuk et al. |
| 2021/0361257 A1 | 11/2021 | Eimer et al. |
| 2021/0370032 A1 | 12/2021 | Fahey et al. |
| 2021/0401418 A1 | 12/2021 | Dang et al. |
| 2022/0008014 A1 | 1/2022 | Rowe et al. |
| 2022/0039670 A1 | 2/2022 | Berrada et al. |
| 2022/0039671 A1 | 2/2022 | Fahey |
| 2022/0117555 A1 | 4/2022 | Zarbatauy et al. |
| 2022/0118228 A1 | 4/2022 | Fahey et al. |
| 2022/0142652 A1 | 5/2022 | Alexander et al. |
| 2022/0143368 A1* | 5/2022 | Pulugurtha ............ A61B 17/22 |
| 2022/0151618 A1 | 5/2022 | Eigler et al. |
| 2022/0167861 A1 | 6/2022 | Stahmann |
| 2022/0184355 A1 | 6/2022 | Fahey et al. |
| 2022/0192677 A1 | 6/2022 | Wedul et al. |
| 2022/0218355 A1 | 7/2022 | Wedul et al. |
| 2022/0218964 A1 | 7/2022 | Fahey et al. |
| 2022/0226000 A1 | 7/2022 | Alexander et al. |
| 2022/0226623 A1 | 7/2022 | Fahey et al. |
| 2022/0240856 A1 | 8/2022 | Stahmann et al. |
| 2022/0265280 A1 | 8/2022 | Chamorro et al. |
| 2022/0313426 A1* | 10/2022 | Gifford, III ........... A61F 2/2418 |
| 2023/0056924 A1 | 2/2023 | Fox et al. |
| 2023/0084193 A1 | 3/2023 | Fahey et al. |
| 2023/0118243 A1 | 4/2023 | Fox et al. |
| 2023/0129883 A1 | 4/2023 | Andriola et al. |
| 2023/0158280 A1 | 5/2023 | Andriola et al. |
| 2023/0165672 A1 | 6/2023 | Fahey et al. |
| 2023/0191094 A1 | 6/2023 | Fahey et al. |

(56) References Cited

U.S. PATENT DOCUMENTS

| | | | |
|---|---|---|---|
| 2023/0200667 A1 | 6/2023 | Andriola et al. |
| 2023/0201546 A1 | 6/2023 | Fahey et al. |
| 2023/0240852 A1 | 8/2023 | Fahey et al. |
| 2023/0371953 A1 | 11/2023 | Pantages et al. |
| 2023/0372683 A1 | 11/2023 | Andriola et al. |

FOREIGN PATENT DOCUMENTS

| | | |
|---|---|---|
| AU | 2011332324 | 6/2013 |
| AU | 2012214279 | 8/2013 |
| AU | 2018228451 | 9/2019 |
| CA | 2785041 | 8/2011 |
| CA | 2786575 | 8/2011 |
| CA | 2818417 | 5/2012 |
| CA | 2955389 | 1/2016 |
| CA | 3054891 | 9/2018 |
| CN | 101415452 | 4/2009 |
| CN | 102458316 | 5/2012 |
| CN | 102905626 | 1/2013 |
| CN | 103458832 | 12/2013 |
| CN | 105662653 | 6/2016 |
| CN | 106456308 | 2/2017 |
| CN | 109646063 A | 4/2019 |
| CN | 110536657 | 12/2019 |
| EP | 1112044 | 1/2007 |
| EP | 2097012 | 9/2009 |
| EP | 2528646 | 12/2012 |
| EP | 2642954 | 10/2013 |
| EP | 2967867 | 1/2016 |
| EP | 3087953 | 11/2016 |
| EP | 3291773 | 3/2018 |
| EP | 3300672 | 4/2018 |
| EP | 3329860 | 6/2018 |
| EP | 3579907 | 12/2019 |
| EP | 3589238 | 1/2020 |
| EP | 3624701 | 3/2020 |
| EP | 2999412 | 5/2020 |
| EP | 3705154 | 9/2020 |
| EP | 3716877 | 10/2020 |
| EP | 3740163 | 11/2020 |
| EP | 3766431 | 1/2021 |
| EP | 3834737 | 6/2021 |
| EP | 3843618 | 7/2021 |
| EP | 3871626 | 9/2021 |
| EP | 3886761 | 10/2021 |
| EP | 3893731 | 10/2021 |
| EP | 3897369 | 10/2021 |
| IL | 176973 | 12/2006 |
| IL | 221127 | 9/2012 |
| IL | 226374 | 7/2013 |
| IL | 2115975 | 11/2016 |
| IL | 227756 | 6/2017 |
| IL | 220201 | 8/2017 |
| IL | 253648 | 9/2017 |
| IL | 255379 | 12/2017 |
| IL | 252395 | 4/2020 |
| IN | 2011KN04472 | 7/2012 |
| IN | 2012KN01275 | 2/2013 |
| IN | 2013KN01954 | 11/2013 |
| IN | 2013CN06525 | 8/2014 |
| IN | 2012KN01988 | 8/2016 |
| JP | 2007527742 | 10/2007 |
| JP | 2010508093 | 3/2010 |
| JP | 2012196504 | 10/2012 |
| JP | 2013046784 | 3/2013 |
| JP | 2014503246 | 2/2014 |
| JP | 2014512869 | 5/2014 |
| JP | 2020509812 | 4/2020 |
| KR | 20010046155 | 6/2001 |
| WO | WO99029227 | 6/1999 |
| WO | WO2003028522 | 4/2003 |
| WO | WO2005074367 | 8/2005 |
| WO | WO2007083288 | 7/2007 |
| WO | WO2008055301 | 5/2008 |
| WO | WO2010128501 | 11/2010 |
| WO | WO2010129089 | 11/2010 |
| WO | WO2011093941 | 8/2011 |
| WO | WO2011094521 | 8/2011 |
| WO | WO2012071075 | 5/2012 |
| WO | WO2012085913 | 6/2012 |
| WO | WO2012109557 | 8/2012 |
| WO | WO2013014539 | 1/2013 |
| WO | WO2013096965 | 6/2013 |
| WO | WO2014091222 | 6/2014 |
| WO | WO2014150106 | 9/2014 |
| WO | WO2014188279 | 11/2014 |
| WO | WO2016014821 | 1/2016 |
| WO | WO2016038115 | 3/2016 |
| WO | WO2016178171 | 11/2016 |
| WO | WO2018024868 | 2/2018 |
| WO | WO2018132549 | 7/2018 |
| WO | WO2018158747 | 9/2018 |
| WO | WO2019186101 | 2/2019 |
| WO | WO2019142152 | 7/2019 |
| WO | WO2019175401 | 9/2019 |
| WO | WO2019179447 | 9/2019 |
| WO | WO2019188917 | 10/2019 |
| WO | WO2019189079 | 10/2019 |
| WO | WO2019209420 | 10/2019 |
| WO | WO2020023514 | 1/2020 |
| WO | WO2020094085 | 5/2020 |
| WO | WO2020094087 | 5/2020 |
| WO | WO2020094094 | 5/2020 |
| WO | WO2020110048 | 6/2020 |
| WO | WO2020123338 | 6/2020 |
| WO | WO2020132678 | 6/2020 |
| WO | WO2020142515 | 7/2020 |
| WO | WO2020142613 | 7/2020 |
| WO | WO2020198694 | 10/2020 |
| WO | WO2020202046 | 10/2020 |
| WO | WO2020206366 | 10/2020 |
| WO | WO2020215090 | 10/2020 |
| WO | WO2020217194 | 10/2020 |
| WO | WO2020219265 | 10/2020 |
| WO | WO2020225698 | 11/2020 |
| WO | WO2020225757 | 11/2020 |
| WO | WO2020229636 | 11/2020 |
| WO | WO2020234751 | 11/2020 |
| WO | WO2020251700 | 12/2020 |
| WO | WO2020259492 | 12/2020 |
| WO | WO2021025905 | 2/2021 |
| WO | WO2021026485 | 2/2021 |
| WO | WO2021046753 | 3/2021 |
| WO | WO2021050589 | 3/2021 |
| WO | WO2021055264 | 3/2021 |
| WO | WO2021065873 | 4/2021 |
| WO | WO2021065874 | 4/2021 |
| WO | WO2021065875 | 4/2021 |
| WO | WO2021065912 | 4/2021 |
| WO | WO2021072315 | 4/2021 |
| WO | WO2021086707 | 5/2021 |
| WO | WO2021091566 | 5/2021 |
| WO | WO2021096766 | 5/2021 |
| WO | WO2021101707 | 5/2021 |
| WO | WO201126699 | 6/2021 |
| WO | WO2021113670 | 6/2021 |
| WO | WO2021136252 | 7/2021 |
| WO | WO2021136261 | 7/2021 |
| WO | WO2021138041 | 7/2021 |
| WO | WO2021146342 | 7/2021 |
| WO | WO2021150765 | 7/2021 |
| WO | WO2021158559 | 8/2021 |
| WO | WO2021159001 | 8/2021 |
| WO | WO2021162888 | 8/2021 |
| WO | WO2021178636 | 9/2021 |
| WO | WO2021190547 | 9/2021 |
| WO | WO2021212011 | 10/2021 |
| WO | WO2021216964 | 10/2021 |
| WO | WO2021217055 | 10/2021 |
| WO | WO2021217059 | 10/2021 |
| WO | WO2021224736 | 11/2021 |
| WO | WO2022046921 | 3/2022 |
| WO | WO2022076601 | 4/2022 |
| WO | WO2022081980 | 4/2022 |

(56) References Cited

FOREIGN PATENT DOCUMENTS

| WO | WO2022103973 | 5/2022 |
|---|---|---|
| WO | WO2022192280 | 9/2022 |
| WO | WO2022266465 | 12/2022 |
| WO | WO2022266503 | 12/2022 |
| WO | WO2022272131 | 12/2022 |
| WO | WO2023278725 | 1/2023 |

OTHER PUBLICATIONS https://www.ahdictionary.com/word/search.html?q=actuator. Accessed Oct. 18, 2023.*
https://www.dictionary.com/browse/Actuator. Accessed Oct. 18, 2023.*
International Search Report and Written Opinion received for International Application No. PCT/US22/19374, filed Mar. 8, 2022; Applicant: Shifamed Holdings, LLC; Date of Mailing: Jun. 24, 2022; 11 pages.
Jodi Perkins, "Corvia Medical and physIQ Partner in Global Phase 3 Heart Failure Clinical Trial to Leverage Novel Digital Endpoints," Press Release, 2019 Copyright, Medical Alley Association, 3 pages.
Lehner et al., "The Creation of an Interatrial Right-To-Left Shunt in Patients with Severe, Irreversible Pulmonary Hypertension: Rationale, Devices, Outcomes," Current Cardiology Reports (2019) 21: 31, https://doi.org/10.1007/s11886-019-1118-8; 9 pages.
International Search Report and Written Opinion received for International Application No. PCT/US19/69106 filed Dec. 31, 2019; Applicant: Shifamed Holdings, LLC; Date of Mailing: Mar. 23, 2020; 10 pages.
International Search Report and Written Opinion received for International Application No. PCT/US20/49996 filed Sep. 9, 2020; Applicant: Shifamed Holdings, LLC; Date of Mailing: Feb. 17, 2021; 16 pages.
International Search Report and Written Opinion received for International Application No. PCT/US20/063360 filed Dec. 4, 2020; Applicant: Shifamed Holdings, LLC; Date of Mailing: Apr. 5, 2021; 13 pages.
International Search Report and Written Opinion received for International Application No. PCT/US20/64529 filed Dec. 11, 2020; Applicant: Shifamed Holdings, LLC; Date of Mailing: Apr. 8, 2021; 12 pages.
International Search Report and Written Opinion received for International Application No. PCT/US19/68354, filed Dec. 23, 2019; Applicant: Shifamed Holdings, LLC; Date of Mailing: Mar. 17, 2020; 11 pages.
International Search Report and Written Opinion received for International Application No. PCT/US21/16932, filed Feb. 5, 2021; Applicant: Shifamed Holdings, LLC; Date of Mailing: Jun. 3, 2021; 11 pages.
International Search Report and Written Opinion received for International Application No. PCT/US21/14433, filed Jan. 21, 2021; Applicant: Shifamed Holdings, LLC; Date of Mailing: May 14, 2021; 16 pages.
International Search Report and Written Opinion received for International Application No. PCT/US21/28926, filed Apr. 23, 2021 ; Applicant: Shifamed Holdings, LLC; Date of Mailing: Jul. 22, 2021; 16 pages.
International Search Report and Written Opinion received for International Application No. PCT/US20/12059, filed Jan. 2, 2020; Applicant: Shifamed Holdings, LLC; Date of Mailing: Jun. 5, 2020; 12 pages.
International Search Report and Written Opinion received for International Application No. PCT/US20/25509, filed Mar. 27, 2020; Applicant: Shifamed Holdings, LLC; Date of Mailing: Jun. 25, 2020; 9 pages.
International Search Report and Written Opinion received for International Application No. PCT/US20/26738, filed Apr. 3, 2020; Applicant: Shifamed Holdings, LLC; Date of Mailing: Jun. 30, 2020; 8 pages.
International Search Report and Written Opinion received for International Application No. PCT/US21/28931, filed Apr. 23, 2021; Applicant: Shifamed Holdings, LLC; Date of Mailing: Sep. 24, 2021; 20 pages.
International Search Report and Written Opinion received for International Application No. PCT/US21/27747, filed Apr. 16, 2021 ; Applicant: Shifamed Holdings, LLC; Date of Mailing: Oct. 1, 2021; 16 pages.
International Search Report and Written Opinion received for International Application No. PCT/US21/53836, filed Oct. 6, 2021; Applicant: Shifamed Holdings, LLC; Date of Mailing: Jan. 25, 2022; 20 pages.
International Search Report and Written Opinion received for International Application No. PCT/US21/47573, filed Aug. 25, 2021; Applicant: Shifamed Holdings, LLC; Date of Mailing: Feb. 3, 2022; 15 pages.
Kocaturk, O. et al., "Whole shaft visibility and mechanical performance for active MR catheters using copper-nitinol braided polymer tubes," Journal of Cardiovascular Magnetic Resonance. Aug. 12, 2009, vol. 11, No. 29, pp. 9, col. 1, In 5-6.
Hossain, M. et al. "In situ preparation of graphene-ZnO composites for enhanced graphite exfoliation and graphene-nylon-6 composite films," Journal of Applied Polymer Science, Dec. 5, 2016, vol. 134, No. 27, p. 8, In 15-16,.
International Search Report and Written Opinion received for International Application No. PCT/US21/55191, filed Oct. 15, 2021; Applicant: Shifamed Holdings, LLC; Date of Mailing: Mar. 1, 2022; 12 pages.
Anomet Products "Conductive Nitinol Wire" Aug. 15, 2020 (Aug. 15, 2020) Retrieved from website <URL: https://helpx.adobe.com/acrobat/using/allow-or-block-links-internet.html?mv=product&mv2=acrobat>, 4 pages.
International Search Report and Written Opinion received for International Application No. PCT/US21/58996, filed Nov. 11, 2021; Applicant: Shifamed Holdings, LLC; Date of Mailing: Feb. 7, 2022; 23 pages.
International Search Report and Written Opinion received for International Application No. PCT/US22/35764, filed Jun. 30, 2022; Applicant: Shifamed Holdings, LLC; Date of Mailing: Sep. 19, 2022; 10 pages.
International Search Report and Written Opinion received for International Application No. PCT/US22/34027, filed Jun. 17, 2022; Applicant: Shifamed Holdings, LLC; Date of Mailing: Oct. 25, 2022; 8 pages.
International Search Report and Written Opinion received for International Application No. PCT/US22/34995, filed Jun. 24, 2022; Applicant: Shifamed Holdings, LLC; Date of Mailing: Nov. 18, 2022; 17 pages.
Perk et al., "Catheter-based left atrial appendage occlusion procedure: role of echocardiography," published on behalf of the European Society of Cardiology, Sep. 8, 2011, 7 pages.
Collado et al, "Left Atrial Appendage Occlusion for Stroke Prevention in Nonvalvular Atrial Fibrillation," Journal of the American Heart Association, Jun. 2021, 18 pages.
Ando et al., "Left ventricular decompression through a patent foramen ovale in a patient with hypertrophic cardiomyopathy: a case report," Cardiovascular Ultrasound vol. Article No. 2 (2004).
Braunwald, Heart Disease, Chapter 6, 2015, p. 186.
Bridges et al., "The Society of Thoracic Surgeons practice guideline series: transmyocardial laser revascularization," The Annals of Thoracic Surgery, vol. 77, Issue 4, Apr. 2004, pp. 1494-1502.
Bristow et al., "Improvement in cardiac myocyte function by biological effects of medical therapy: a new concept in the treatment of heart failure," European Heart Journal, vol. 16, Issue suppl. F, Jul. 1995, pp. 20-31.
Case et al., "Relief of High Left-Atrial Pressure in Left-Ventricular Failure," Lancet, Oct. 17, 1964, pp. 841-842.
Coats et al., "Controlled trial of physical training in chronic heart failure. Exercise performance, hemodynamics, ventilation, and autonomic function," Circulation, 1992;85:2119-2131.

(56) References Cited

OTHER PUBLICATIONS

Davies et al., "Reduced contraction and altered frequency response of isolated ventricular myocytes from patients with heart failure," Circulation, (1995), 92:2540-2549, Circulation, (1995), 92:2540-2549.

Ennezat et al., "An unusual case of low-flow, low gradient severe aortic stenosis: Left-to-right shunt due to atrial septal defect," Cardiology, (2009), 113(2):146-148.

Ewert et al., "Masked Left Ventricular Restriction in Elderly Patients With Atrial Septal Defects: a Contraindication for Closure," Catheterization and Cardiovascular Interventions, 52: 177-180, 2001.

Ewert et al., "Acute left heart failure after interventional occlusion of an atrial septal defect," Z. Kardiol., Catheterization and Cardiovascular Interventions, Z. Kardiol., (May 2001), 90(5):362-366.

Geiran et al., "Changes in cardiac dynamics by opening an interventricular shunt in dogs," J. Surg. Res., (Jan. 1990), 48(1):6-12.

Gelernter-Yaniv et al., "Transcatheter closure of left-to-right interatrial shunts to resolve hypoxemia," Congenit. Heart Dis., (Jan. 2008), 31(1):47-53.

Gewillig et al., "Creation with a stent of an unrestrictive lasting atrial communication," Cardio. Young, (2002), 12(4):404-407.

Khositseth et al., "Transcatheter Amplatzer Device Closure of Atrial Septal Defect and Patent Foramen Ovale in Patients With Presumed Paradoxical Embolism," Mayo Clinic Proc., 79:35-41 (2004).

Kramer et al., "Controlled study of captopril in chronic heart failure: a rest and exercise hemodynamic study," Circulation, (1983), 67(4):807-816.

Lai et al., "Bidirectional shunt through a residual atrial septal defect after percutaneous transvenous mitral commissurotomy," Cardiology, (1993), 83(3):205-207.

Lemmer et al., "Surgical implications of atrial septal defect complicating aortic balloon valvuloplasty," Ann. thorac. Surg., (Aug. 1989), 48(2):295-297.

Park et al., "Blade atrial septostomy: collaborative study," Circulation, 66(2):258-266 (1982).

Roven et al., "Effect of Compromising Right Ventricular Function in Left Ventricular Failure by Means of Interatrial and Other Shunts," American Journal Cardiology, 24:209-219 (1969).

Salehian et al., "Improvements in Cardiac Form and Function After Transcatheter Closure of Secundum Atrial Septal Defects," Journal of the American College of Cardiology, 45(4):499-504 (2005).

Schmitto et al., "Chronic heart failure induced by multiple sequential coronary microembolization in sheep," The International Journal of Artificial Organs, 31(4):348-353 (2008).

Schubert et al., "Left ventricular conditioning in the elderly patient to prevent congestive heart failure after transcatheter closure of the atrial septal defect," Catheter Cardiovasc. Interv., (2005), 64(3):333-337.

Stormer et al., "Comparative study of in vitro flow characteristics between a human aortic valve and a designed aortic and six corresponding types of prosthetic heart valves," European Surgical Research, (1976), 8(2):117-131.

Stumper et al., "Modified technique of stent fenestration of the atrial septum, Heart," (2003), 89:1227-1230.

Trainor et al., "Comparative Pathology of an Implantable Left Atrial Pressure Sensor," ASAIO Journal, Clinical Cardiovascular/Cardiopulmonary Bypass, 59(5):486-92 (2013).

Zhou et al., "Unidirectional valve patch for repair of cardiac septal defects with pulmonary hypertension," Annals of Thoracic Surgeons, 60: 1245-1249, 1995.

Extended European Search Report received for Application No. 20896031.0, Applicant: Shifamed Holdings, LLC; Date of Mailing: Dec. 7, 2023; 11 pages.

Huang et al., "Shape Memory Materials," Science Direct, Materials Today, vol. 13, Sep. 1, 2010, 15 pages.

Retrieved from the Internet:URL:https://www.sciencedirect.com/science/article/pii/S1369702110701280#bib1, retrieved on Jan. 22, 2024, 1 page.

Extended European Search Report received for Application No. 21791938.0, Applicant: Shifamed Holdings, LLC; Date of Mailing: Apr. 3, 2024; 6 pages.

* cited by examiner

SHAPE MEMORY ACTUATORS FOR ADJUSTABLE SHUNTING SYSTEMS, AND ASSOCIATED SYSTEMS AND METHODS

CROSS-REFERENCE TO RELATED APPLICATION(S)

This application is a 35 U.S.C. § 371 U.S. National Phase application of International Patent Application No. PCT/US2022/019374, filed Mar. 8, 2022, which claims the benefit of U.S. Provisional Application No. 63/158,508, filed Mar. 9, 2021, the disclosures of which are incorporated herein by reference in their entireties.

TECHNICAL FIELD

The present technology is generally directed to shape memory actuators for adjustable shunting systems.

BACKGROUND

Implantable shunting systems are widely used to treat a variety of patient conditions by shunting fluid from a first body region/cavity to a second body region/cavity. The flow of fluid through the shunting systems is primarily controlled by the pressure gradient across the shunt lumen and the geometry (e.g., size) of the shunt lumen. One challenge with conventional shunting systems is selecting the appropriate geometry of the shunt lumen for a particular patient. A lumen that is too small may not provide enough therapy to the patient, while a lumen that is too large may create new issues in the patient. Despite this, most conventional shunts cannot be adjusted once they have been implanted. Accordingly, once the system is implanted, the therapy provided by the shunting system cannot be adjusted or titrated to meet the patient's individual needs.

As a result of the above, shunting systems with adjustable lumens have recently been proposed to provide a more personalized or titratable therapy. Such systems enable clinicians to titrate the therapy to an individual patient's needs, as well as adjust the therapy over time as the patient's disease changes. Adjustable shunting systems, however, generally require a power source (e.g., energy) to drive the adjustments. For example, the shunting system may include an implanted energy storage component such as a battery for storing energy that can subsequently be released to adjust a geometry of the shunt. However, depending on where the shunting system is positioned, the size of, and thus the storage capacity of, an implanted energy storage component may be limited. Accordingly, a need exists to provide adjustable shunting systems that can be adjusted using as little energy as possible.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

Figure 1:
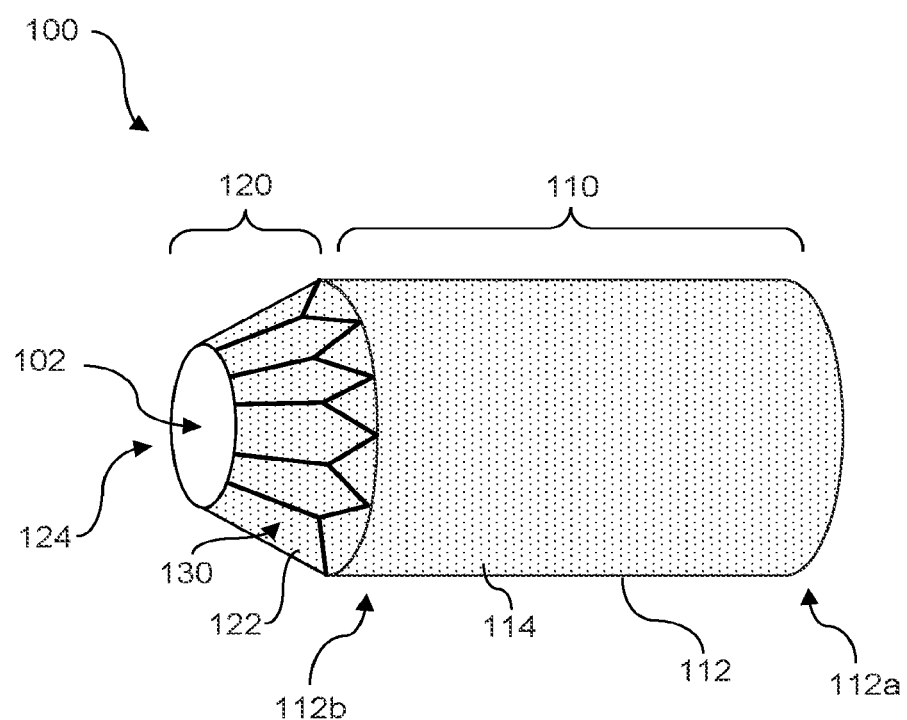
FIG. 1 is a schematic illustration of an adjustable shunting system configured in accordance with select embodiments of the present technology.

The present technology is directed to adjustable shunting systems having shape memory actuators and associated systems and methods. In some embodiments, for example, the present technology provides an adjustable shunting system having a first region and a second region. The first region includes a shunting element configured to extend between a first body region and a second body region. The second region is coupled to the first region and includes a shape memory actuator having a plurality of struts proximate the shunting element and a plurality of projections extending from the plurality of struts. A lumen extends through the first region and the second region between a first orifice and a second orifice. In operation, the shape memory actuator can be used to adjust a geometry of the lumen, the first orifice, and/or the second orifice in vivo to adjust the flow of fluid through the shunting system. Of note, the system is configured such that (1) mechanical strain in the shape memory actuator is concentrated in the struts, and (2) resistive heating preferentially occurs in the struts and not the projections, e.g., because the projections are not electrically in series with the struts. As described in detail herein, such a configuration is expected to advantageously reduce the energy requirements needed to actuate the shape memory actuator and, therefore, the energy requirements needed to adjust flow through the shunting system.

Shape memory actuators can be used to make in vivo adjustments to a geometry of an implanted shunting system. For example, shape memory actuators can be thermally actuated by heating at least a portion of the actuator to induce a geometric change in the actuator, which can be translated into a geometric change in the shunt lumen and/or lumen orifice. Examples of shape memory actuators and adjustable shunting systems utilizing shape memory actuators are described in U.S. patent application Ser. No. 17/016,192, filed Sep. 9, 2020, and International Patent Application No. PCT/US2020/063360, filed Dec. 4, 2020, the disclosures of which are incorporated by reference herein in their entireties.

To actuate shape memory actuators, an energy storage component (e.g., a battery, capacitor, etc.) in electrical communication with the shape memory actuator can release stored energy in the form of electrical current. The electrical current can flow through and resistively heat the shape memory actuator. If the shape memory actuator is heated above a "transition temperature," a material phase change occurs (e.g., the shape memory actuator transitions from a low-temperature martensitic material state to a high-temperature R-phase or austenitic material state). The amount of energy required to resistively heat the actuator above its transition temperature depends on a number of factors, including the mass, resistance, and transition temperature of the actuator. Moreover, the amount of energy that can be stored by the energy storage components may be limited based the size of the energy storage component, which itself may be limited by patient anatomy. It is therefore beneficial to reduce/minimize the amount of energy required to resistively heat the actuator or targeted portions of the actuator above its transition temperature to ensure the energy storage component can store sufficient energy to actuate the actuator for a desired period of operation. In some embodiments, the energy that enables an actuation of a shape memory actuator is applied directly (e.g., from a source outside of the body) to the actuator or to an electrical circuit in electrical communication with the actuator without the use of an implanted energy storage component. In such examples, reducing/minimizing the amount of energy required to resistively heat the actuator or targeted portions of the actuator will nevertheless be beneficial because it will accelerate an adjustment procedure and perhaps increase the safety and cost-effectiveness of the procedure.

The present technology therefore provides shape memory actuators that are designed to be actuated using relatively low amounts of energy. For example, as described in detail below, the shape memory actuators are designed such that thermo-mechanically-recoverable strain in the actuator is concentrated in a select region of the actuator rather than being distributed evenly throughout the actuator. As a result, only the portion(s) of the actuator having the concentrated recoverable strain needs to be resistively heated in order to cause the actuator to undergo a complete, or nearly complete, geometry change related to the shape memory effect. In addition, the actuator is designed such that when an electrical current is applied to the actuator, the electrical current flows preferentially through regions of the actuator experiencing strain, thereby preferentially heating these portions of the actuator. Without being bound by theory, this is expected to reduce the amount of energy required to actuate the shape memory actuator.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the claims but are not described in detail with respect to FIGS. 1-6B. In various respects, the terminology used to describe shape memory behavior may adopt the conventions described in ASTM F2005 (Standard Terminology for Nickel-Titanium Shape Memory Alloys). Although the terminology adopted herein is from Nickel-Titanium alloys, it is understood that the disclosure is not limited to Nickel-Titanium alloys (e.g., Ti—Nb, Ni—Ti—Cu, Co—Al—Ni, Ag—Cd, Au—Cd, and various polymeric shape memory materials may be substituted).

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

As used herein, the use of relative terminology, such as "about", "approximately", "substantially" and the like refer to the stated value plus or minus ten percent. For example, the use of the term "about 100" refers to a range of from 90 to 110, inclusive. In instances in which the context requires otherwise and/or relative terminology is used in reference to something that does not include a numerical value, the terms are given their ordinary meaning to one skilled in the art.

As used herein, the term "geometry" can include the size and/or the shape of an element. Accordingly, when the present disclosure describes a change in geometry, it can refer to a change in the size of an element (e.g., moving from a smaller circle to a larger circle), a change in the shape of an element (e.g., moving from a circle to an oval), and/or a change in the shape and size of an element (e.g., moving from a smaller circle to a larger oval). In various embodiments, "geometry" refers to the relative arrangements and/or positions of elements in the respective system.

FIG. 1 is a schematic illustration of an adjustable shunting system 100 ("the system 100") configured in accordance with select embodiments of the present technology. The system 100 includes a first region 110, a second region 120, and a lumen 102 extending through the first region 110 and the second region 120 for transporting fluid. For example, when the system 100 is implanted in a patient, the system 100 can transport (e.g., drain) fluid from a first body region (not shown) to a second body region (not shown) via the lumen 102. For example, in embodiments in which the system 100 is an interatrial shunting system, the lumen 102 can transport blood between a left atrium to a right atrium of a patient's heart when implanted across a septal wall of the patient.

The first region 110 is configured to at least partially interface with patient tissue when the system 100 is implanted in a patient. For example, the first region 110 can include a shunting element or frame 112 that can traverse patient tissue (e.g., the septal wall) when implanted in the patient. The shunting element 112 has a first end portion 112a that is in fluid communication with the first body region (e.g., the left atrium) when the system 100 is implanted and a second end portion 112b that is in fluid communication with the second body region (e.g., the right atrium) when the system 100 is implanted. The lumen 102 extends through the shunting element 112, permitting fluid to flow between the first end portion 112a and the second end portion 112b through an interior of the shunting element 112. In some embodiments, the shunting element 112 includes a first membrane 114 at least partially encasing or integral with the shunting element 112. The first membrane 114 can be composed of a biocompatible and/or anti-thrombogenic material, such as PTFE, ePTFE, PET (e.g., Dacron), silicone, urethane, nylon, or the like.

The second region 120 can have a generally tapered (e.g., conical or hyperboloid) shape extending from the first region 110 to an orifice 124 (e.g., an outflow aperture or an inflow aperture). The lumen 102 extends through the second region 120 and fluidly couples an interior of the second region 120 with the interior of the first region 110. Accordingly, when the system 100 is implanted in a patient, fluid may flow into the lumen 102 via an orifice (not shown) at the first end portion 112a, through the lumen 102 extending through both the first region 110 and the second region 120, and out of the orifice 124 defined by the second region 120. In other embodiments, the direction of fluid flow may be reversed, such that fluid flows into the lumen 102 via the orifice 124. In some embodiments, the second region 120 is configured to at least partially extend into the second body region (e.g., the right atrium) when the system 100 is implanted in a patient. Accordingly, at least a portion of the second region 120 may be out of contact with patient tissue (e.g., extending into/suspended in the patient's right atrium). Moreover, although shown as having the second region 120 coupled to the second end portion 112b of the shunting element 112, in other embodiments the second region 120 can be coupled to the first end portion 112a of the shunting element 112 such that the second region 120 extends into the first body region (e.g., the left atrium).

The second region 120 includes an actuator 130 and a second membrane 122. As described in detail below with respect to FIGS. 2A-3, the actuator 130 is configured to adjust a geometry of the orifice 124 to change the flow of fluid through the lumen 102, enabling a clinician to selectively adjust the level of therapy provided by the system 100. The second membrane 122 can encase or otherwise be coupled to the actuator 130. The second membrane 122 can be composed of a biocompatible, anti-thrombogenic, and/or at least partially flexible material, such as PTFE, ePTFE, PET (e.g., Dacron), silicone, urethane, nylon, or the like.

The system 100 can include other components not illustrated in FIG. 1. For example, the system 100 can optionally include one or more anchors for securing the system 100 to patient tissue (which may either be integral with, or a separate component coupled to, the shunting element 112), one or more energy storage components (e.g., batteries, capacitors, etc.), one or more energy receiving components (e.g., antenna, inductive elements, etc.), one or more active components (e.g., sensors), or the like. The foregoing components may be generally similar to those described in International Patent Application No. PCT/US2020/063360, previously incorporated by reference herein.

Figure 2A:
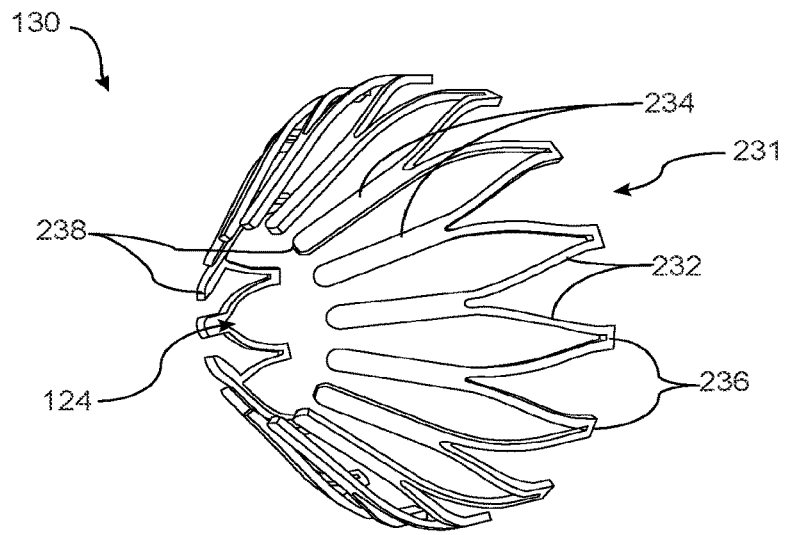
FIGS. 2A-2C are isometric, side, and front views, respectively, of an actuator of the adjustable shunting system shown in FIG. 1 and configured in accordance with select embodiments of the present technology.
Figure 2B:
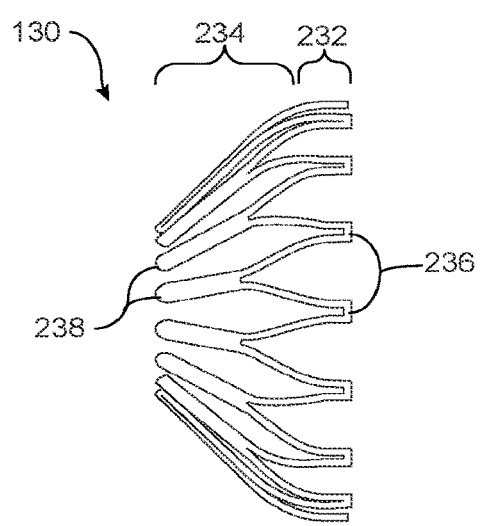
Figure 2C:
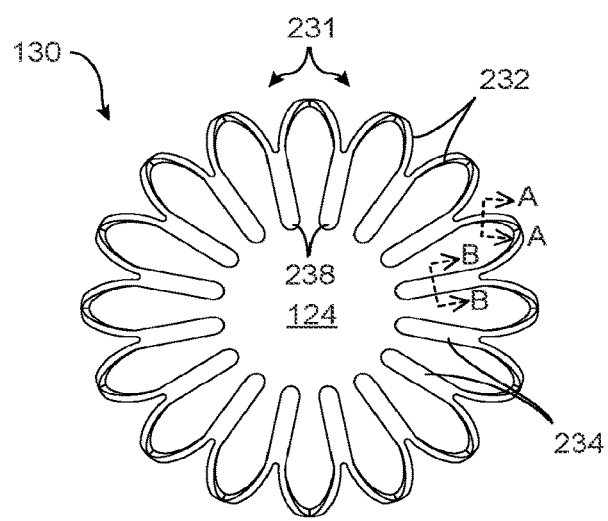

FIGS. 2A-2C are isometric, side, and front views, respectively, of the actuator 130, with the other components of the system 100 omitted for clarity. Referring collectively to FIGS. 2A-2C, the actuator 130 includes a plurality of actuation segments or members 231, with each individual actuation member 231 having a strut portion 232 and a projection portion 234. In some embodiments, individual actuation members 231 have a general Y-shape (with the struts 232 forming the upper portion of the "Y" and the projection 234 forming the lower portion of the "Y"), and can be arranged side-by-side to form an annular/conical shape of the actuator 130. The actuation members 231 can be integral with one another such that the actuator 130 is a single unitary component.

The strut portions of the actuation members 231 therefore collectively comprise a plurality of struts 232 and the projection portions of the actuation members 231 therefore collectively comprise a plurality of projections 234. As illustrated, the plurality of struts 232 form a partially curved annular, conical, hyperbolic, or ring-like shape, and the plurality of projections extend at least partially radially inward from the plurality of struts 232 to form the conical/funnel shape. Although the struts 232 are shown as having a "zig-zag" pattern, the struts 232 can also have a diamond-shaped or other suitable pattern while still having the partially curved annular shape. A proximal end portion 236 of the struts can be secured to the shunting element 112 (FIG. 1) or other component of the system 100. As described in greater detail below, the actuator 130 can be configured to "hinge" or otherwise bend at the struts 232 during actuation of the actuator 130.

The projections 234 are elongated fingers/levers that extend from a distal end portion of the struts 232. In the embodiment shown in FIG. 2A, the projections 234 extend radially inward toward a center point of the orifice 124. In other embodiments, the projections 234 may extend in a complex path, e.g., spirally, in a general direction toward the orifice 124 thereby defining the overall funnel shape. Regardless, a distal end portion 238 of the projections 234 therefore at least partially defines the geometry of the orifice 124. In some embodiments, the projections 234 are integral with the struts 232 such that the actuator 130 is a single unitary structure. For example, the actuator 130 can be fabricated as a unitary component, e.g., by forming the actuator 130 from a single piece of material. As described in greater detail below, the actuator 130 can be configured such that the projections do not bend during actuation of the actuator 130.

Figure 2D:
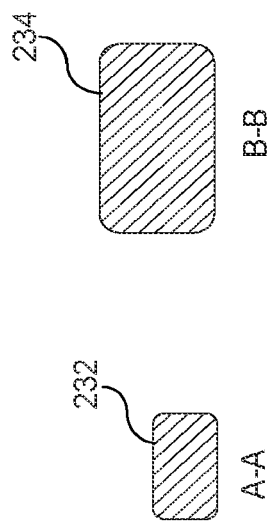
FIG. 2D is a schematic of a cross-sectional area of the actuator of FIGS. 2A-2C taken along the lines indicated in FIG. 2C.

The struts 232 and the projections 234 may have different dimensions. For example, the struts 232 can have an axial cross-sectional area that is less than an axial cross-sectional area of the projections 234. FIG. 2D, for example, provides a schematic representation of an axial cross-sectional area of a strut 232 (taken along the lines A-A shown in FIG. 2C) and an axial cross-sectional area of a projection 234 (taken along the lines B-B shown in FIG. 2C). In other embodiments, the struts 232 can have the same or even a greater axial cross-sectional area than the projections 234. Although shown as having a generally rectangular cross-sectional shape, the struts 232 and/or the projections 234 can have other suitable cross-sectional shapes, such as round, oval, triangular, pentagonal, or the like.

The cross-sectional area of the struts 232 can be at least 10% smaller than the cross-sectional area of the projections 234. For example, the cross-sectional area of the struts 232 can be at least 10% smaller than, at least 20% smaller than, at least 50% smaller than, at least 75% smaller than, or at least 99% smaller than the cross-sectional area of the projections 234. Such an arrangement can facilitate resistive heating of the struts 232 while maintaining desirable mechanical properties associated with relatively larger projections 234. In some embodiments, the cross-sectional area of the struts 232 can vary along a length of the struts 232, but is nevertheless generally smaller than the cross-sectional area of the projections 234. Likewise, the cross-sectional area of the projections 234 can vary along a length of the projections 234, but is nevertheless generally larger than the cross-sectional area of the struts 232. As described in detail below, struts 232 that have a small cross-section beneficially increases the electrical resistance of the struts 232 relative to struts with a larger cross-section, which can assist with resistive heating. In some embodiments (e.g., those driven by a current source) a smaller cross-section strut can increase an electrical current density in the struts 232 during resistive heating of the actuator 130.

In embodiments in which the actuator 130 is fabricated as a unitary structure, the actuator 130 can be initially fabricated with uniform dimensions (e.g., the cross-sectional area of the struts 232 is equal to the cross-sectional area of the projections 234). The struts 232 can then be reduced in cross-sectional area relative to the projections 234 during a manufacturing operation (e.g., localized grinding, micro-blasting, milling, ablating, cutting, chemical etching electro-polishing, etc.). In other embodiments, the actuator 130 is initially fabricated such that the struts 232 and the projections 234 have different cross-sectional areas without the need for the cross-sectional-reduction manufacturing operation.

The actuator 130 can be configured to adjust a geometry (e.g., dimension) of the orifice 124. In particular, the actuator 130 can be at least partially composed of a shape memory material, such as nitinol. The actuator 130 (or a portion thereof) can therefore be transitionable between a first material phase or state (e.g., martensitic, R-phase, a composite state between martensitic and R-phase, etc.) and a second material phase or state (e.g., austenitic, R-phase, a composite state between austenitic and R-phase, etc.) by heating the actuator 130 above its transition temperature. In the first material state, the actuator 130 may be deformable (e.g., plastic, compressible, expandable, etc.). In the second material state, the actuator 130 may exhibit superelastic properties and/or have a preference toward a specific preferred geometry (e.g., original geometry, fabricated geometry, heat-set geometry, shape-set geometry, etc.). If the actuator 130 is deformed relative to its preferred geometry when in the first material state, heating the actuator 130 above its transition temperature causes the actuator 130 to move to and/or toward its preferred geometry as it transitions to its second material state. In some embodiments, the actuator 130 is fabricated to have a transition temperature greater than average body temperature such that, during and after implantation in a patient, the actuator 130 remains in the first material phase.

Figure 2E:
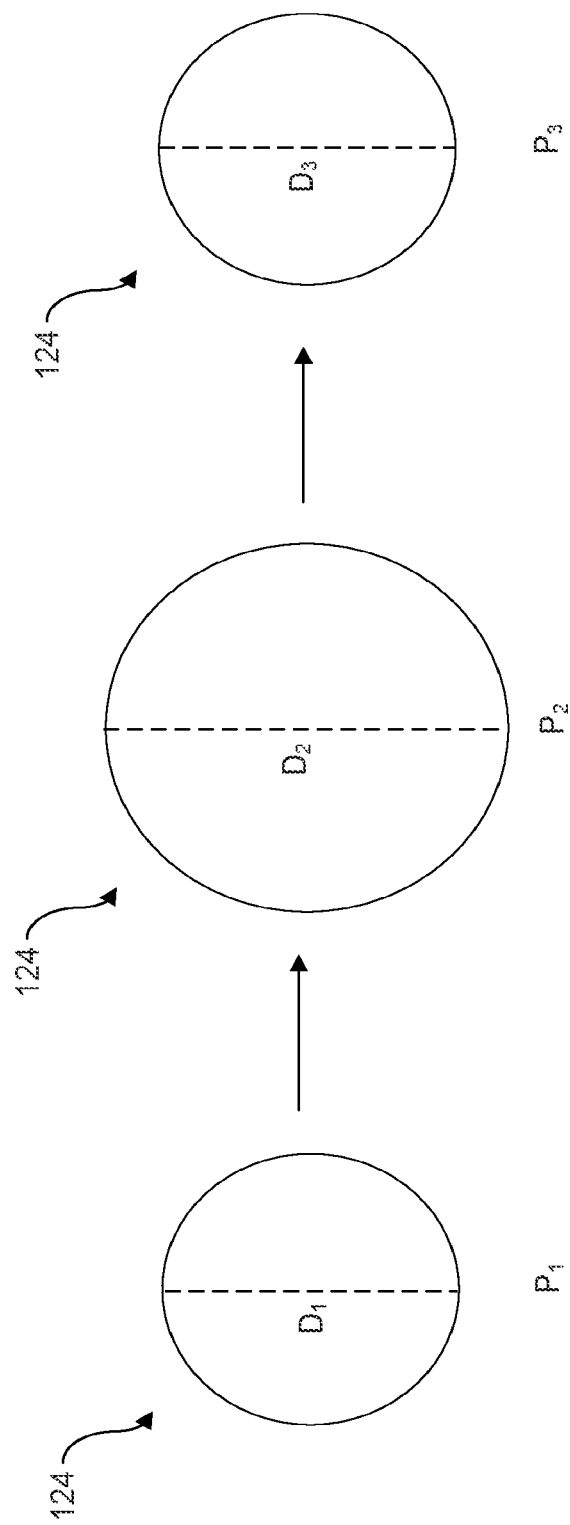
FIG. 2E is a series of schematic illustrations depicting an orifice size of the adjustable shunting system shown in FIG. 1 in various configurations.

FIG. 2E is a series of representative configurations of the orifice 124—which is defined by the distal end portion 238 of the projections 234 (FIGS. 2A-2C)—that can be attained by adjusting the actuator 130. In particular, FIG. 2E illustrates a first configuration $P_1$ in which the orifice 124 has a first diameter $D_1$. In some embodiments, the first configuration $P_1$ corresponds to the preferred geometry of the actuator 130. In other embodiments, the first configuration $P_1$ corresponds to an initial deformed configuration of the actuator 130 (e.g., following the initial coupling of the actuator 130 to the shunting element 212 (FIG. 1), following manipulation of the actuator 130 into a slim-profile delivery configuration, etc.). The orifice 124 can be transitioned to a second configuration $P_2$ having a second diameter $D_2$ greater than the first diameter $D_1$ by, for example, mechanically expanding the actuator 130. For example, a balloon can be inserted into an interior of the second region 120 of the system 100 and inflated to expand the second region 120. During this operation, the actuator 130 is deformed relative to its preferred geometry and the distal end portion 238 of the projections 234 are pushed radially outward as the second region 120 is expanded. Because the actuator 130 is in the first (e.g., generally deformable) material state, the actuator 130 can largely or entirely retain this expanded configuration even after the deforming force is removed (e.g., the balloon is deflated).

From the second configuration $P_2$, the orifice 124 can be reduced in size by heating the actuator 130 (or a portion thereof) above its transition temperature. Because the actuator 130 is deformed relative to its preferred geometry, heating the actuator 130 above its transition temperature causes the actuator 130 to move to and/or toward its preferred geometry. This draws the distal end portion 238 of the projections 234 radially inward, reducing the size of the orifice 124. For example, heating the actuator 130 above its transition temperature can cause the orifice 124 to assume a third configuration $P_3$ having a third diameter $D_3$ that is less than the second diameter $D_2$. In some embodiments, the third diameter $D_3$ may be the same as the first diameter $D_1$, although in other embodiments the third diameter $D_3$ is greater than or less than the first diameter $D_1$. Although only three configurations are shown, in some embodiments the actuator 130 may be manipulated into other configurations having different orifice 124 dimensions. In some embodiments, heating the actuator 130 (or a portion thereof) can further increase the size of orifice 124—e.g., the third configuration $P_3$ is associated with a third diameter $D_3$ that is larger than both $D_2$ and $D_1$.

In some embodiments, the actuator 130 is deformed relative to its preferred geometry when coupled to the shunting element 112 or other component of the system 100 (FIG. 1) (e.g., during a manufacturing step). In other embodiments, the actuator 130 is not deformed relative to its preferred geometry when coupled to the shunting element 112, but is subsequently deformed via balloon expansion or another manipulation. Regardless, deforming the actuator 130 is achieved by mechanical stress which induces a thermo-elastically-recoverable strain in the actuator 130. The strain, and consequently the geometry of the actuator 130, can be thermally-recovered via a shape memory effect by heating the actuator 130 above its transition temperature such that it transitions to the second material state. The actuator 130 can be heated above its transition temperature via resistive heating or other suitable techniques.

Figure 3:
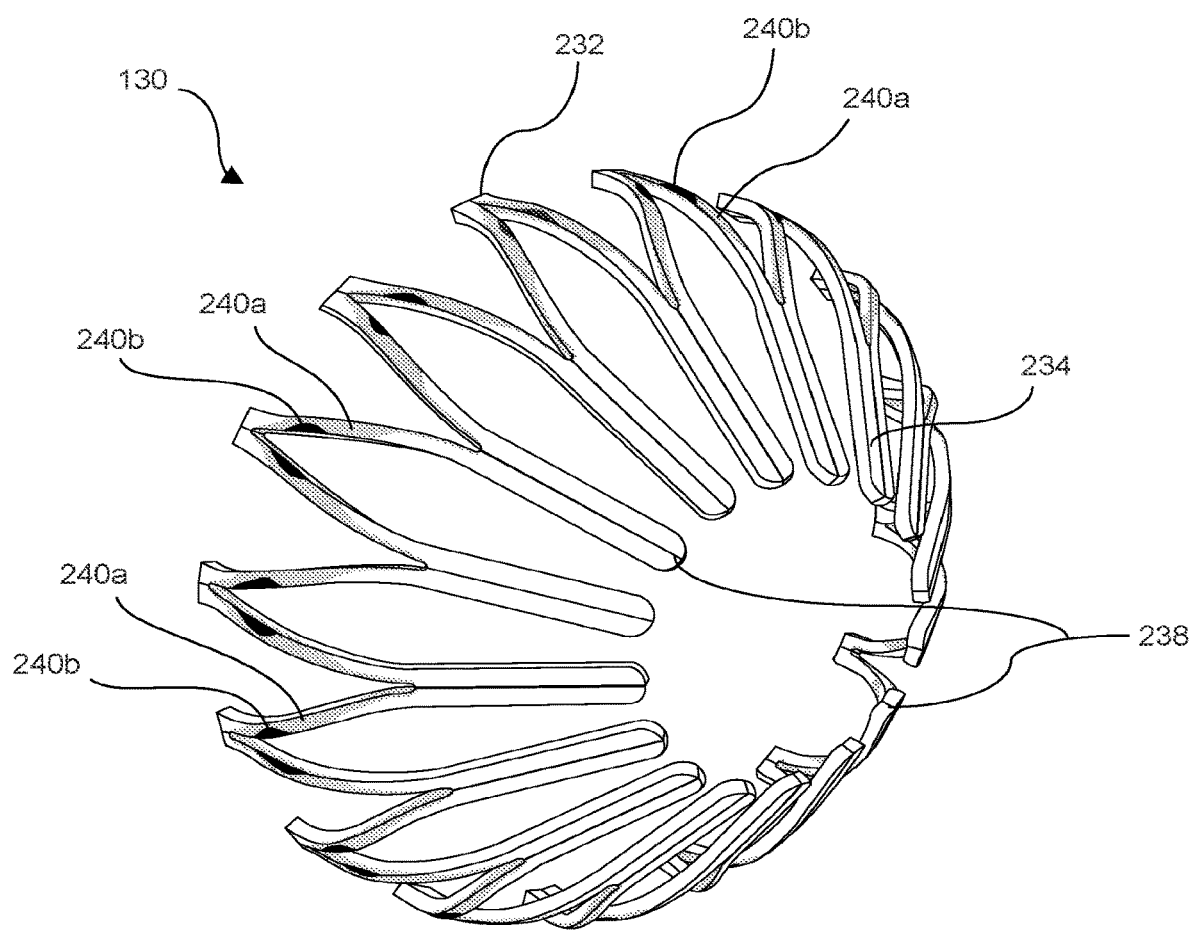
FIG. 3 is a schematic illustration depicting strain in the actuator of FIGS. 2A-2C when the actuator is deformed relative to its preferred geometry in accordance with select embodiments of the present technology.

The actuator 130 can be configured to reduce/minimize the energy requirements needed for actuation. For example, the actuator 130 can be configured such that, when coupled to the shunting element 112 (FIG. 1) and deformed relative to its preferred geometry, all or substantially all of the strain in the actuator 130 associated with this deformation is concentrated in the struts 232. For example, considering a total volume of material in the actuator 130, concentrated strain in the struts 232 can comprise about 60%, about 70%, about 80%, or about 90% of the volumetric fraction of strain in the actuator 130. In some embodiments, concentrated strain in the struts 232 can comprise about 90% to about 98% of the volumetric fraction of strain in the actuator 130. In embodiments, the strain may be localized further to a smaller region within the struts 232 by varying the cross-sectional geometry. FIG. 3, for example, is an illustration of the distribution of strain in the actuator 130 when the actuator 130 is deformed relative to its preferred geometry. As illustrated by increasing strain values from a first region 240a having a first strain value to a second region 240b with a second, higher strain value at or near the proximal end portions 236 of the struts 232, all or at least substantially all of the strain is in the struts 232, with little to no strain in the projections 234. As illustrated by the concentration of strain within the strut 232, (the second region 240b shown as the black regions/spots in FIG. 3), the strain can be further localized by varying the cross-section of the strut 232 along its length. Of note, the actuator 130 is designed such that the strain in the actuator 130 remains concentrated in the struts 232 during operation of the actuator 130, regardless of the position or orientation of the actuator 130. For example, even as the actuator 130 is further deformed relative to its preferred geometry, the strain remains concentrated in the struts 232. This can be accomplished by forming the actuator 130 such that the struts 232 operate as a "hinge", in which any deformation of the actuator 130 occurs via bending or flexing at the struts 232.

Because the strain is concentrated in the struts 232, only the struts 232 need to be heated above the transition temperature to move the actuator toward its preferred geometry. In other words, because there is little to no strain in the projections 234, the projections 234 need not be heated above the transition temperature, since there is little to no deformation in the projections 234 to be recovered. Without being bound by theory, concentrating the strain to a particular region of the actuator 130 is expected to provide several advantages relative to an actuator having strain distributed throughout a majority of its structure. For example, concentrating strain in the struts 232 reduces the volume of material that must be heated above a transition temperature in order to actuate the actuator 130. In turn, when coupled with systems and methods that enable preferential heating of the strained regions of the structure, this reduces the energy requirements needed to actuate the actuator 130, as limited to no energy would need to be delivered to unstrained areas. This is of particular importance for implanted medical devices having a finite energy storage capacity and/or energy receiving capabilities.

Even though the strain is concentrated in the struts 232, inducing a material phase change (and a corresponding geometric change) in the struts 232 moves the projections 234 because the projections 234 are coupled to (e.g., integral with) the struts 232. In fact, due to their elongated length, a relatively small angular movement in the struts 232 can be translated into a relatively larger angular movement of the distal end portions 238 of the projections 234. Because the distal end portions 238 define the orifice 124, a relatively small geometric change in the struts 232 can thus impart a relatively larger geometric change in the orifice 124.

In addition to concentrating strain in the struts 232, the actuator 130 can be configured such that the regions with higher strain (e.g., the struts 232) also have a higher degree of resistive heating when a current is applied to the actuator. For example, the projections 234 can be designed such that they are effectively not electrically in series with the struts 232. As a consequence of this, within embodiments, electrical current applied to the actuator will flow primarily or entirely through sections of the actuator 130 that are adjacent (e.g., proximate) to struts 232, thereby imparting the greatest degree of resistive heating at the struts 232. Of course, the projections 234 may still be subject to some degree of conductive heating resulting from the resistive heating of the adjacent struts 232, but such conductive heating does not significantly affect the energy output required to actuate the actuator 130.

The different degree of resistive heating induced in the struts 232 and the projections 234 when an electrical current is applied to the actuator 130 can be achieved by manipulating a variety of factors. In some embodiments, the actuator 130 can be comprised of a single material. In such embodiments, the actuator 130 can be designed such that the struts 232 are electrically in series with one another and that each of the projections 234 is not in electrical series with the struts 232 or other portions of the actuator 130. For example, individual struts of the plurality of struts 232 can be electrically coupled in series, while the plurality of projections 234 are not in electrical series with the plurality of struts 232. In such a configuration, each projection 234 can effectively terminate in an open circuit, preventing substantial current flow (and therefore, meaningful resistive heating) along the projection 234. Within embodiments as described, an electrical power source (e.g., a voltage source, a current source, etc.) can have contact with the actuator 130 in portions that are proximate to struts 232.

In some embodiments, the actuator 130 can be constructed of struts 232 that are comprised of an electrically conductive shape memory material and projections 234 that are comprised of a relatively non-conductive material, such as a plastic. The struts 232 and the projections 234 can be joined in a manufacturing process (e.g., using welding, sutures, adhesives, press-fits, and/or other techniques known to those skilled in the art). In such embodiments, the electrical resistance of the struts 232 can be lower than that of the projections 234, however, without being bound by theory, it is expected that since the projections 234 are essentially non-conductive that they will force substantially all current applied to the actuator 130 to flow through the struts 232. In such a design, the flow of current through the system can additionally or alternatively be dictated by the configuration of the actuator (e.g., whether struts and projections are electrically in series), as described above. In embodiments as described, the plurality of struts is constructed such that the struts are in electrical continuity with one another. In some embodiments, both the struts 232 and the projections 234 are electrically conductive, but are joined during manufacturing through a non-conductive joint that isolates the projections 234 from an electrical circuit that includes the plurality of struts 232. In each of the foregoing examples, the actuator 130 design effectively removes the projections 234 from an electrical circuit that is used to heat the actuator 130, meaning that all or substantially all energy applied to the actuator 130 will travel through struts 232 (which as previously described contains substantially all the strain in the component). As such, the energy requirements are reduced relative to embodiments in which the electrical current must flow through the entirety of actuator 130 in order to elevate the temperature of the struts 232.

Figure 4:
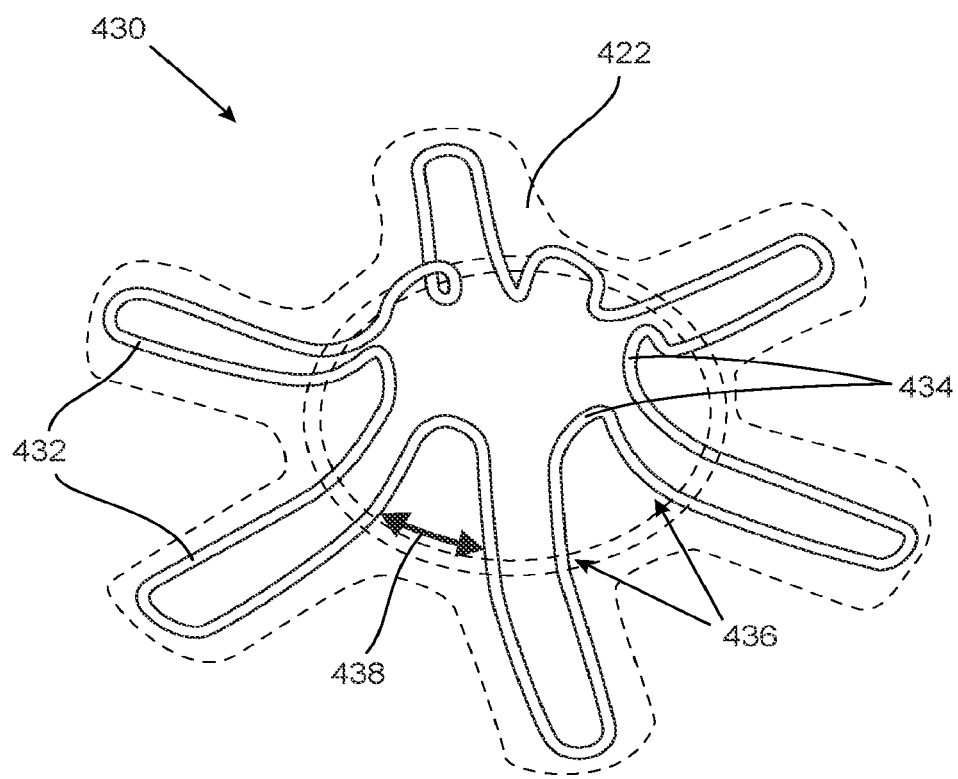
FIG. 4 is a partially isometric view of another actuator configured in accordance with select embodiments of the present technology.

Although described in the context of struts and projections, the shape memory actuators described herein can include other suitable designs that (1) concentrate mechanical strain in the shape memory actuator in a particular region or portion of the actuator, and (2) cause resistive heating of the actuator to preferentially occur in said particular region or portion with the strain. For example, FIG. 4 illustrates an actuator 430 coupled to a membrane 422 and configured in accordance with select embodiments of the present technology. The actuator 430 and the membrane 422 can be coupled to the first region 110 of the system 100, e.g., in lieu of the second region 120 of the system 100 described with reference to FIGS. 1-3.

The actuator 430 can be composed of a shape-memory wire or filament (e.g., nitinol wireform) embedded within or otherwise affixed to the membrane 422, which may be the same or generally similar to the membrane 122 described with reference to FIG. 1. In alternative embodiments, the actuator 430 may not be integrated with or functionally coupled to a membrane. In the illustrated embodiment, the actuator 430 is formed to have a plurality of first petals or loops 432, a plurality of second petals or loops 434, and a plurality of curved or bent regions 436 positioned between and coupling the plurality of first petals 432 and the plurality of second petals 434. The plurality of first petals 432 can be coupled to an anchoring element or frame of the shunting system (e.g., the shunting element 112, shown in FIG. 1), or otherwise provide mechanical support to the actuator 430. The second petals 434 can extend radially inward from the first petals 432 to form an orifice 424 (e.g., an inflow orifice or an outflow orifice) to a lumen (e.g., the lumen 102, shown in FIG. 1).

The actuator 430 can be configured such that any mechanical strain induced by deforming the actuator 430 relative to its preferred geometry preferentially builds in the curved regions 436, e.g., relative to any mechanical strain induced in the first petals 432 and the second petals 434. That is, when the actuator 430 is deformed relative to its preferred geometry (e.g., via balloon expansion, catheterization, or the like), the actuator 430 bends or hinges at the curved regions 436. As a result, the geometry of the first petals 432 and the second petals 434 remains generally unchanged, but the spatial position of the second petals 434 relative to the first petals 432 and/or relative to each other may change (e.g., thereby changing a dimension of the orifice 424). Likewise, when a previous deformation of the actuator 430 is thermo-elastically recovered (e.g., via actuating the actuator 430), the thermoelastic recovery occurs primarily in the curved regions 436. Because the curved regions 436 are coupled to the first petals 432 and the second petals 436, this recovery may cause the second petals 434 to move relative to the first petals 432 and change a dimension of the orifice 424. This above operation is similar to concentrating mechanical strain in the struts 232 to cause a corresponding movement of the projections 234, described above with respect to the actuator 130.

The actuator 430 can further be configured such that the curved regions 436 can be preferentially heated relative to the first petals 432 and/or the second petals 434 to provide a more efficient shape memory actuator. For example, the actuator 430 can include a series of electrical bridges 438 extending between the curved regions 436 (FIG. 4 only illustrates a single electrical bridge 438, but in some embodiments the actuator 430 can include a plurality of individual electrical bridges 438 extending between individual curved regions 436 so that each individual curved region 438 is coupled to adjacent curved regions 438 by an electrical bridge 438). The electrical bridges 438 can electrically connect the curved regions 436 to form an electrical circuit. In some embodiments, the electrical circuit is electrically isolated from (e.g., not in series with) the first petals 432 and the second petals 434, such that electrical current flowing the electrical circuit preferentially flows through the curved regions 436 and not the first petals 432 or the second petals 434. In some embodiments, this may be accomplished by virtue of any of the techniques described above with respect to concentrating electrical current in, and thus resistive heating of, the struts 232 relative to the projections 234 (e.g., different cross-sectional areas, different materials, etc.). In some embodiments, the curved regions 436 can form an electrical circuit with the first petals 432 but not the second petals 434. In such embodiments, the actuator 430 is still expected to operate more efficiently because even though current flows through the first petals 432, current does not need to flow through (or resistively heat) the second petals 434 to actuate the actuator 430.

As described above, and regardless of whether the actuator 130 (FIGS. 1-3) or the actuator 430 (FIG. 4) is utilized, the system 100 utilizes a shape-memory effect of a shape memory actuator to adjust a geometry of the orifice 124, 424 to control the flow of fluid through the system 100. In the illustrated embodiment, the shape-memory effect can be utilized to reduce a diameter of the orifice 124, 424. To increase the diameter of the orifice 124, 424, a balloon or other instrument must physically interface with the system 100. A variation embodiment of system 100 can be configured inversely, where a shape-memory effect can be utilized to increase a diameter of an orifice 124, 424, and another instrument can physically interface with system 100 to reduce the diameter of orifice 124, 424. Accordingly, both examples of the system 100 described above can be said to have a "uni-directional shape memory adjustment mechanism."

However, in some embodiments, the present technology provides systems having a "bi-directional shape memory adjustment mechanism" in which a shape-memory effect can be utilized to both increase and decrease a diameter or other dimension of a system orifice or lumen. For example, FIGS. 5A-5H illustrate an actuation assembly 500 for use with a shunting system and configured in accordance with select embodiments of the present technology. As described in detail below, the actuation assembly 500 provides a bi-directional shape memory adjustment mechanism. In some embodiments, the actuation assembly 500 can be used with the system 100 instead of the actuator 130.

The actuation assembly 500 includes a first actuator 530 and a second actuator 540. The first actuator 530 can be generally similar to the actuator 130 described with respect to FIGS. 1-3 and can include a plurality of struts 532 and a plurality of projections 534. The second actuator 540 can also be generally similar to the actuator 130 and can include a plurality of struts 542 and a plurality of projections 544. However, the second actuator 540 has a different preferred geometry than the first actuator 530.

Figure 5A:
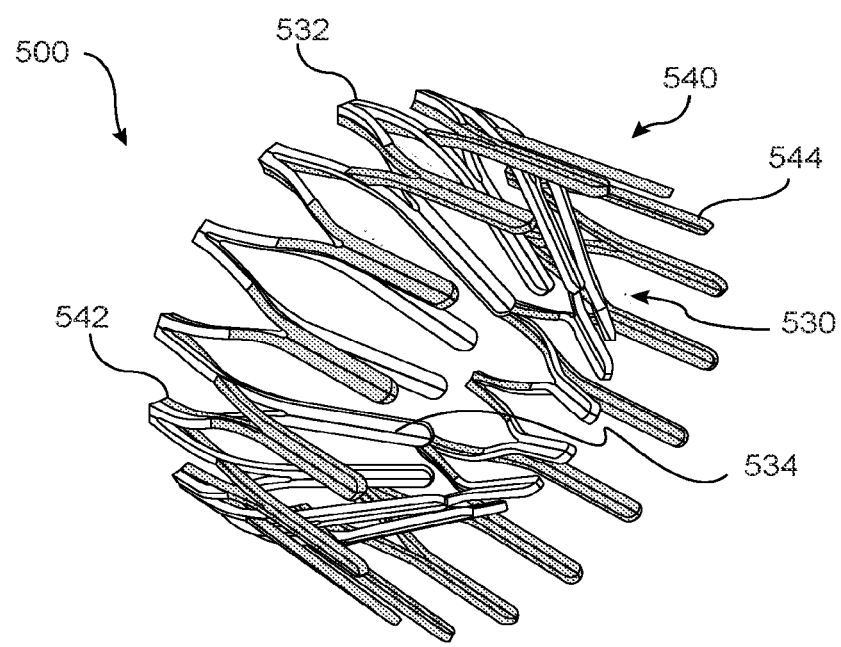
FIGS. 5A-5H are a series of illustrations depicting an actuation assembly having two actuators for use with an adjustable shunting system and configured in accordance with select embodiments of the present technology.
Figure 5B:
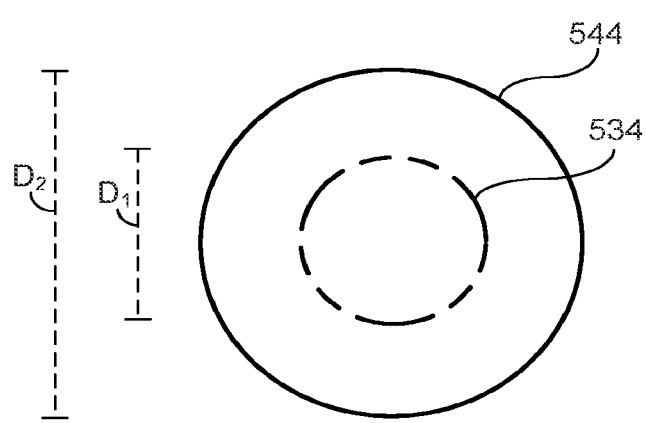

FIG. 5A shows the actuation assembly 500 in an uncoupled state to illustrate the preferred geometry of the first actuator 530 and the preferred geometry of the second actuator 540. It should be noted that FIG. 5A has been drawn to clearly illustrate the preferred geometries of each actuator relative to one another and to show the approximate assembled spatial relationship, but for ease of visualization does not show a representative coupling or integration of the two actuators or of their struts 532 and 542. FIG. 5B is a schematic representation of an orifice defined by a distal end region of the projections 534 and 544, respectively, and corresponding to the configuration shown in FIG. 5A. As shown in FIGS. 5A and 5B, the first actuator 530 (i.e., the projections 534) defines an orifice having a first diameter $D_1$ when in its preferred geometry, while the second actuator 540 (i.e., the projections 544) defines an orifice having a second diameter $D_2$ that is greater than the first diameter $D_1$ when in its preferred geometry.

Figure 5C:
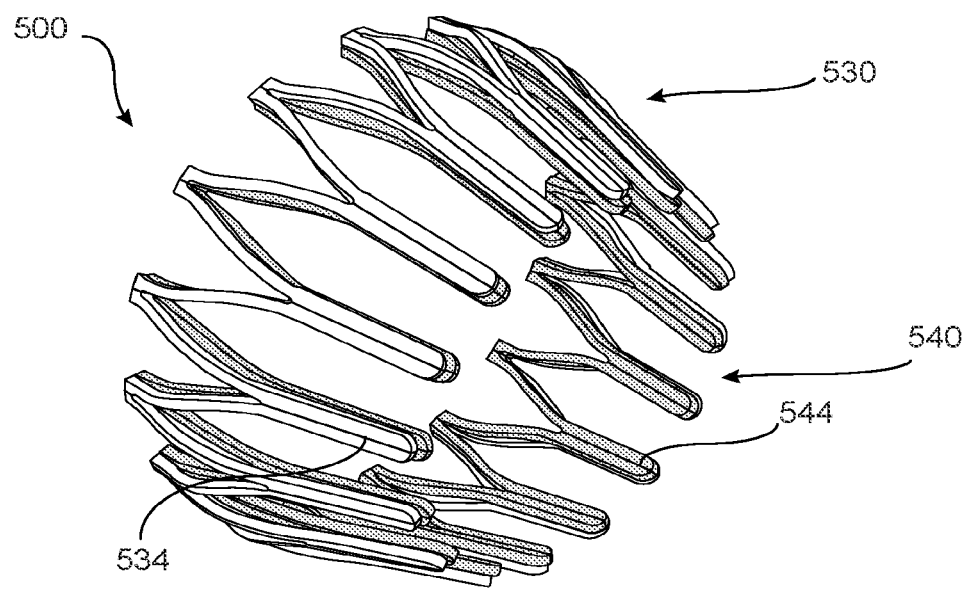
Figure 5D:
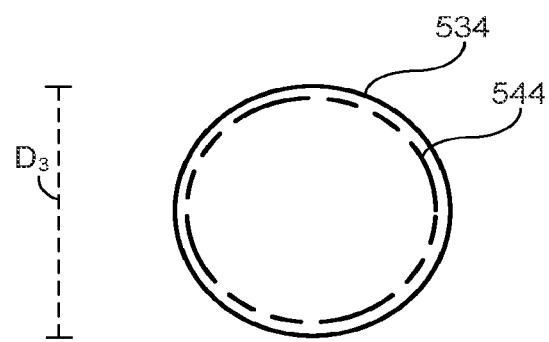

To form the actuation assembly 500, the first actuator 530 is coupled to the second actuator 540, as shown in FIG. 5C. For example, the struts 532 of the first actuator 530 can be coupled to the struts 542 of the second actuator, and the projections 534 of the first actuator 530 can be coupled to the projections 544 of the second actuator 540. The first actuator 530 can be coupled to the second actuator 540 by welding, gluing, suturing, stapling, or other suitable techniques for adhering one structure to another structure. Coupling the first actuator 530 and the second actuator 540 deforms both the first actuator 530 and the second actuator 540 relative to their preferred geometries. For example, as shown in FIG. 5D, coupling the first actuator 530 and the second actuator 540 causes the actuation assembly 500 to define an orifice having a third diameter $D_3$ that is greater than the first diameter $D_1$ corresponding to the preferred geometry of the first actuator 530 (FIG. 4B) but less than the second diameter $D_2$ corresponding to the preferred geometry of the second actuator 540 (FIG. 5B).

Coupling the first actuator 530 and the second actuator 540 therefore induces strain in both the first actuator 530 and the second actuator 540. As described above with respect to the actuator 130, this strain can be concentrated in the struts 532 and 542, with little to no strain in the projections 534 and 544 (e.g., by virtue of the struts 532, 542 operating as a "hinge"). Because strain exists in both actuators, the actuators can be selectively (e.g., independently) heated to thermally recover the strain and induce a geometric change therein.

Figure 5E:
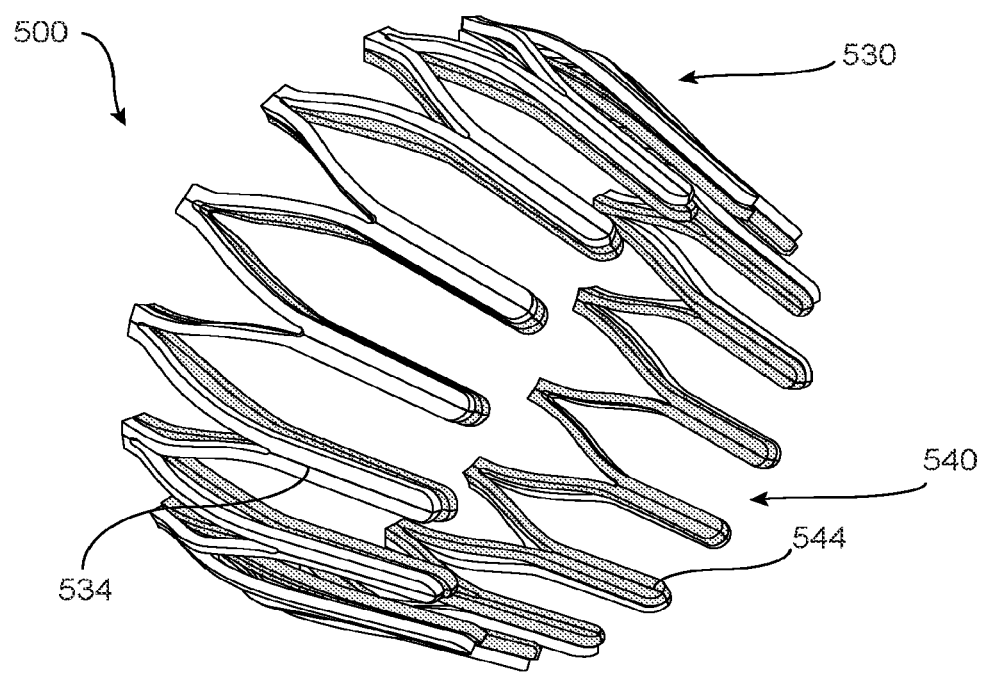
Figure 5F:
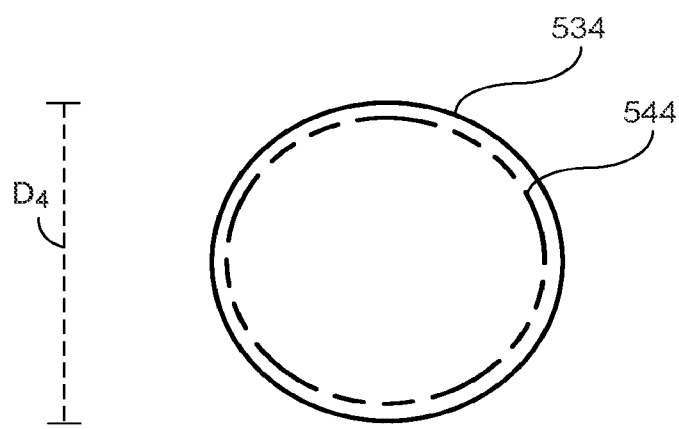

The first actuator 530 and the second actuator 540 are configured to work in opposition. For example, to increase a diameter of the orifice, the second actuator 540 can be selectively actuated (e.g., by resistively heating the struts 542 above a transition temperature). This induces a material phase change in the struts 542 (e.g., transitioning from a martensitic material state or from an R-phase to an R-phase or austenitic material state) and drives the second actuator 540 toward its preferred geometry, as shown in FIG. 5E. Because the first actuator 530 is coupled to the second actuator 540 but remains in the first relatively deformable (e.g., martensitic or R-phase) material state, the first actuator 530 is deformed as it is dragged by the second actuator 540 toward the second actuator's preferred geometry. This causes the orifice to assume a fourth diameter $D_4$, as shown in FIG. 5F. The fourth diameter $D_4$ is greater than the third diameter $D_3$. In some embodiments, the fourth diameter $D_4$ is the same as the second diameter $D_2$ that corresponds to the preferred geometry of the second actuator 540 (FIG. 5B). In other embodiments, the fourth diameter $D_4$ is less than the second diameter $D_2$ due to slight resistance imparted by deformation of the first actuator 530. Following the termination of energy application to the second actuator 540, the struts 542 will cool below a transition temperature and can shift to a different material state (e.g., shift from an austenitic state or an R-phase stat to a martensitic or R-phase state), at which point both first actuator 530 and second actuator 540 can once again be relatively deformable. However, the orifice can entirely or substantially entirely maintain the fourth diameter $D_4$ associated with the actuation of second actuator 540.

Figure 5G:
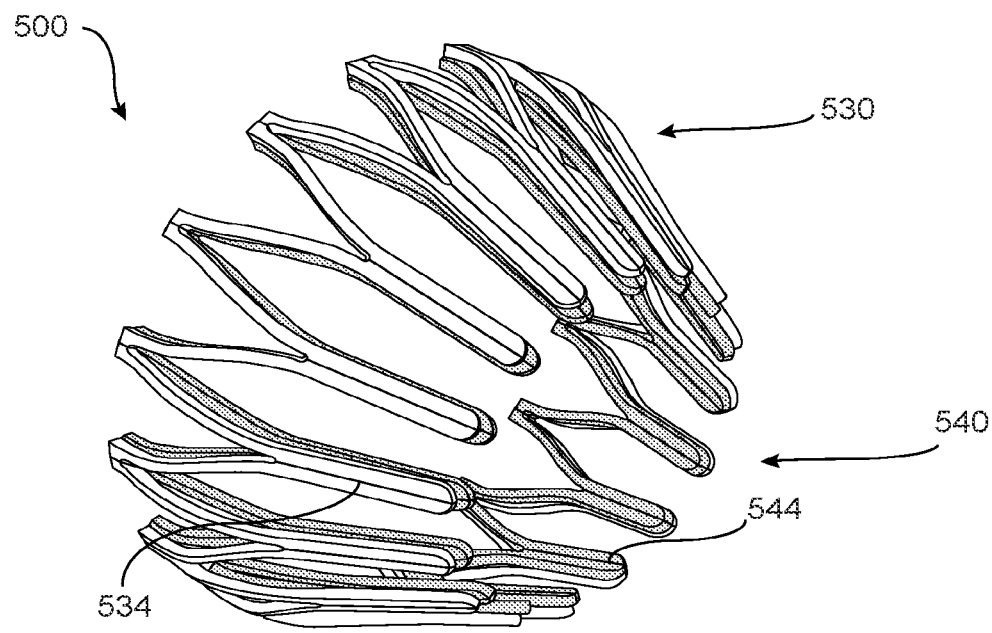
Figure 5H:
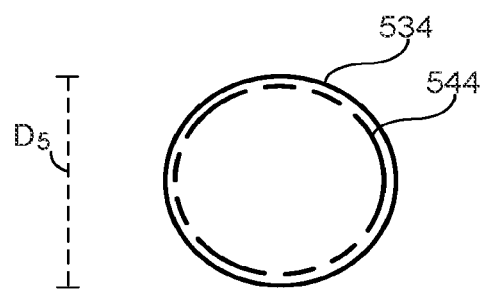

To decrease a diameter of the orifice, the first actuator 530 can be selectively actuated (e.g., by resistively heating the struts 532 above a transition temperature). This induces a material phase change in the struts 532 and drives the first actuator 530 toward its preferred geometry, as shown in FIG. 5G. Because the second actuator 540 is coupled to the first actuator 530 but remains in the first (e.g., martensitic) material state, the second actuator 540 is dragged by the first actuator 530 toward the first actuator's preferred geometry. The causes the orifice to assume a fifth diameter $D_5$, as shown in FIG. 5H. The fifth diameter $D_5$ is less than the third diameter $D_3$. In some embodiments, the fifth diameter $D_5$ is the same as the first diameter $D_1$ that corresponds to the preferred geometry of the first actuator 530 (FIG. 5B). In other embodiments, the fifth diameter $D_5$ is greater than the first diameter $D_1$ due to slight resistance imparted by deformation of the second actuator 540.

To facilitate the selective and independent actuation of the first actuator 530 and the second actuator 540, the first actuator 530 and the second actuator 540 can be electrically and/or thermally isolated. For example, the first actuator 530 may form a first electrical circuit for resistively heating the struts 532, and the second actuator 540 may form a second electrical circuit for resistively heating the struts 542. Additional details regarding operation of opposing "bi-directional" shape memory actuation assemblies are described in U.S. patent application Ser. No. 17/016,192, previously incorporated by reference herein.

As one of skill in the art will appreciate from the disclosure herein, various components of the systems described above can be omitted without deviating from the scope of the present technology. Likewise, additional components not explicitly described above may be added to the systems without deviating from the scope of the present technology. Accordingly, the present technology is not limited to the configurations expressly identified herein, but rather encompasses variations and alterations of the described systems.

For example, although primarily described as having a first section (e.g., the section 110 in FIG. 1) having a shunting element (e.g., shunting element 112 in FIG. 1) that is distinct from a second section (e.g., the section 120 in FIG. 1) having the actuator (e.g., the actuator 130 in FIG. 1), the systems described herein can omit the distinct first section that traverses a patient tissue (e.g., section 110 in FIG. 1). Instead, the entire lumen of the shunt can be defined by an actuation section and any membrane or substrates coupled thereto (e.g., the section 120 in FIG. 1). In such embodiments, a first orifice, second orifice, and lumen associated with the shunt can all be associated with the actuation section. In some examples, a first orifice may be fixed in size and not adjustable, for example through the manner in which an actuation section is secured to and/or integrated with an anchoring feature that holds the device in place in the septal wall. The shunt can contain additional features not related to the lumen or fluid communication channel, such as anchoring features, energy reception, transmission, or storage components, sensors, and other features.

Figure 6A:
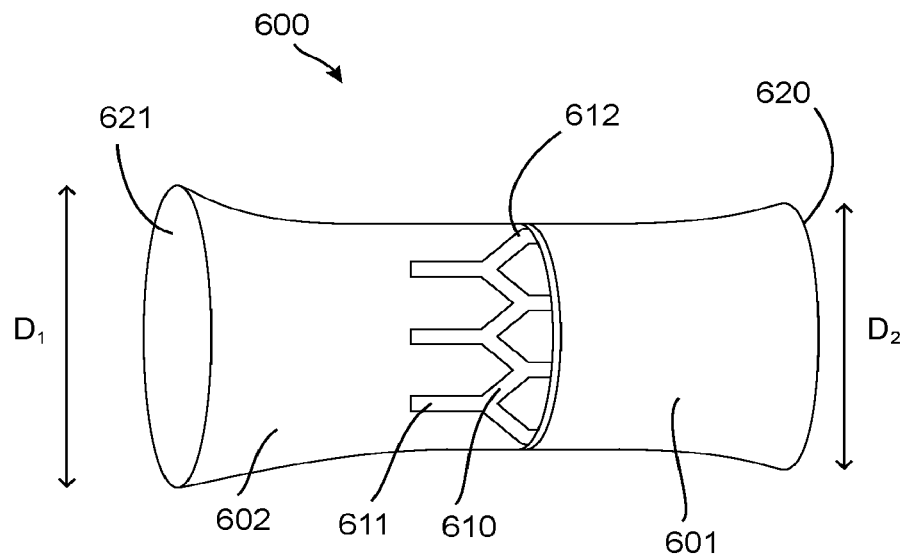
FIGS. 6A and 6B illustrate an adjustable shunting system configured in accordance with select embodiments of the present technology.
Figure 6B:
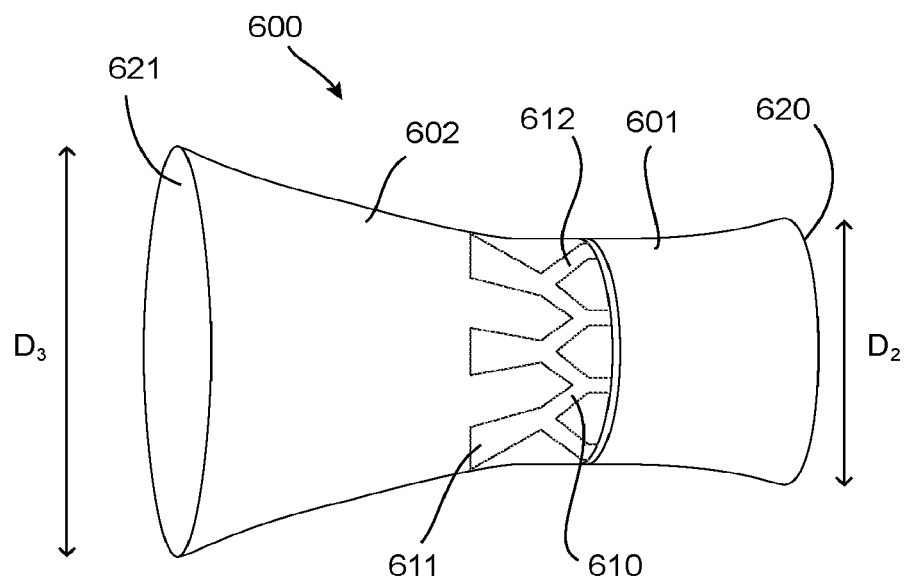

Moreover, in some embodiments the projections of an actuator do not terminate at an orifice, and therefore the terminal/distal ends of the projections may not define an orifice size or geometry directly. For example, some embodiments can use a cone-shaped actuator similar or identical to that shown in FIGS. 2A-4H that is integrated into or otherwise attached to a larger overall structure. In other words, the actuator can be integral to and/or mechanically connected to a portion of a shunt defining a lumen, and therefore exert at least partial control over lumen and/or orifice geometry as described herein without unilaterally defining an orifice of the lumen. An example embodiment is illustrated in FIGS. 6A and 6B. For example, FIGS. 6A and 6B illustrate a shunt 600 that includes a first funnel or flare-shaped end 601 with a first orifice 620 and a second funnel or flare-shared end 602 with a second orifice 621. The shunt 600 can include a frame section (not shown) and a membrane or other substrate 603 that integrates with the frame section in order to define a fluid passageway or lumen between the first orifice 620 and the second orifice 621. The membrane 603 can include sections that are elastic, stretchable, and/or deformable (e.g., in the section associated with second end 602). In a central neck region of the shunt 600, an actuator 610 is mechanically coupled to the frame, the membrane 603, and/or other features that define the lumen of the shunt 600. The actuator 610 can be substantially similar to the actuators described above (e.g., the actuator 130), and include a plurality of struts 612 and a plurality of projections 611. Referring to FIG. 6A, in a first configuration the shunt 600 is configured with the actuator 610 in a first configuration such that the first orifice 620 has a diameter $D_2$ and the second orifice 621 has a diameter $D_1$. The actuator 610 can be actuated via the application of energy as described above, allowing the actuator 610 to move toward a preferred geometry, causing the projections 611 to flare outward. Within embodiments the outward force generated by the geometric change in the projections 611 of actuator 610 can cause the membrane 603 to be stretched or otherwise deformed. Referring to FIG. 6B, the shunt 600 is shown in a second configuration after such a deformation has occurred, with the second orifice 621 having been geometrically altered such that it now has a new diameter $D_3$ that is larger than $D_1$. In this example, the first orifice 620 has been entirely or largely unaffected by actuation of the actuator 610, and retains a diameter $D_2$ that it had while in the first configuration.

The technology described herein can be used in adjustable shunting systems adapted for use at a variety of anatomical locations. For example, in some embodiments the adjustable shunting systems can be interatrial shunts configured to extend through a septal wall and shunt blood from a left atrium to a right atrium. In other embodiments, the adjustable shunting systems can be positioned at another location, such as to provide blood flow between other chambers and passages of the heart or other parts of the cardiovascular system. For example, the systems described herein can be used to shunt blood between the left atrium and the coronary sinus, or between the right pulmonary vein and the superior vena cava, or from the right atrium to the left atrium. In yet other embodiments, the adjustable shunting systems may be used to shunt fluid between other body regions.

EXAMPLES

Several aspects of the present technology are set forth in the following examples:

1. An adjustable shunting system, comprising:
   a first region comprising a shunting element; and
   a second region coupled to the first region, the second region including a shape memory actuator having a plurality of struts proximate the shunting element and a plurality of projections integral with and extending from the plurality of struts; and
   a lumen extending through the first region and the second region between a first orifice and a second orifice,
   wherein the shape memory actuator is configured to adjust a geometry of the lumen, the first orifice, and/or the second orifice, and
   wherein the system is configured such that strain in the shape memory actuator is concentrated in the plurality of struts when the shape memory actuator is deformed relative to its preferred geometry.

2. The adjustable shunting system of example 1 wherein the shape memory actuator is configured such that, when an electrical current is applied to the shape memory actuator, the plurality of struts experiences higher resistive heating than the plurality of projections.

3. The adjustable shunting system of example 2 wherein:
   individual struts of the plurality of struts are in electrical series, and
   the plurality of projections are not in electrical series with the plurality of struts.

4. The adjustable shunting system of any of examples 1-3 wherein the plurality of struts have an axial cross-sectional area smaller than an axial cross-sectional area of the plurality of projections.

5. The adjustable shunting system of any of examples 1-4 wherein, when electrical current flows through the shape memory actuator, the plurality of struts have a higher electrical current density than the plurality of projections.

6. The adjustable shunting system of any of examples 1-5 wherein the plurality of struts form an annular structure, and wherein the plurality of projections extend from the annular structure to form a conical structure.

7. The adjustable shunting system of any of examples 1-6 wherein the plurality of struts are slightly curved.

8. The adjustable shunting system of any of examples 1-7 wherein the plurality of projections are straight.

9. The adjustable shunting system of any of examples 1-8 wherein, when actuated, the shape memory actuator is configured to bend at the struts.

10. The adjustable shunting system of any of examples 1-9 wherein a first end portion of the plurality of projections is coupled to the plurality of struts, and wherein a second end portion of the plurality of struts defines the first orifice.

11. The adjustable shunting system of any of examples 1-10 wherein the plurality of projections are substantially unstrained when the actuator is deformed relative to its preferred geometry.

12. The adjustable shunting system of any of examples 1-11 wherein the plurality of struts and the plurality of projections comprise a unitary structure.

13. The adjustable shunting system of any of examples 1-12 wherein the shape memory actuator is a first shape memory actuator, the struts are first struts, and the projections are first projections, and wherein the second region further comprises:
   a second shape memory actuator coupled to the shunting element and having a plurality of second struts and a plurality of second projections, wherein the second shape memory actuator is configured such that strain in the second shape memory actuator is concentrated in the plurality of second struts when the second shape memory actuator is deformed relative to its preferred geometry,
   wherein the second shape memory actuator is configured to adjust the system in a manner generally opposite that of the first shape memory actuator.

14. The adjustable shunting system of example 13 wherein the first shape memory actuator is configured to increase a dimension of the lumen, the first orifice, and/or the second orifice, and wherein the second shape memory actuator is configured to decrease a dimension of the lumen, the first orifice, and/or the second orifice.

15. The adjustable shunting system of example 13 or example 14 wherein the first shape memory actuator is coupled to the second shape memory actuator, and wherein, when coupled, at least one of the first shape memory actuator and the second shape memory actuator is deformed relative to their respective preferred geometries.

16. The adjustable shunting system of any of examples 1-15 wherein the system is configured such that, when the system is implanted in a patient:
   the shunting element engages patient tissue and extends between a first body region and a second body region;
   the second region extends into the first body region or the second body region; and
   the first orifice is positioned in the first body region and the second orifice is positioned in the second body region.

17. An adjustable shunting system, comprising:
   a first region comprising a shunting element;
   a second region coupled to the first region, the second region including a shape memory actuator having a plurality of struts and a plurality of projections integral with and extending from the plurality of struts,
   wherein the shape memory actuator is configured such that the plurality of struts experiences higher resistive heating than the plurality of projections when an electrical current is applied to the shape memory actuator; and a lumen extending through the first region and the second region between a first orifice and a second orifice,
wherein the shape memory actuator is configured to adjust a geometry of the lumen, the first orifice, and/or the second orifice.

18. The adjustable shunting system of example 17 wherein:
individual struts of the plurality of struts are in electrical series, and
the plurality of projections are not in electrical series with the plurality of struts.

19. The adjustable shunting system of example 17 or example 18 wherein the plurality of struts are formed from a first material having a first conductivity, and wherein the plurality of projections are formed from a second material having a second conductivity less than the first conductivity.

20. The adjustable shunting system of any of examples 17-19 wherein the plurality of struts are electrically isolated from the plurality of projections.

21. The adjustable shunting system of any of examples 17-20 wherein the plurality of struts have an axial cross-sectional area smaller than an axial cross-sectional area of the plurality of projections.

22. The adjustable shunting system of example 21 wherein the axial cross-sectional area of the plurality of struts is at least 50% smaller than the axial cross-sectional area of the plurality of projections.

23. The adjustable shunting system of example 21 or example 22 wherein individual struts have a constant cross-sectional area along an axial length thereof.

24. The adjustable shunting system of example 21 or example 22 wherein individual struts have a variable cross-sectional area along an axial length thereof.

25. The adjustable shunting system of any of examples 17-24 wherein, when electrical current flows through the shape memory actuator, the plurality of struts have a higher electrical current density than the plurality of projections.

26. The adjustable shunting system of any of examples 17-25 wherein, when actuated, the shape memory actuator is configured to bend at the struts.

27. The adjustable shunting system of any of examples 17-26 wherein the system is configured such that any strain in the shape memory actuator is concentrated in the plurality of struts.

28. The adjustable shunting system of example 27 wherein the plurality of struts are slightly curved, and wherein the plurality of projections are straight.

29. The adjustable shunting system of example 27 wherein the plurality of struts form an annular structure, and wherein the plurality of projections extend from the annular structure to form a conical structure.

30. The adjustable shunting system of any of examples 17-29 wherein the plurality of struts and the plurality of projections form a unitary structure.

31. The adjustable shunting system of any of examples 17-30 wherein the system is configured such that, when the system is implanted in a patient:
the shunting element engages patient tissue and extends between a first body region and a second body region;
the second region extends into the first body region or the second body region; and
the first orifice is positioned in the first body region and the second orifice is positioned in the second body region.

32. The adjustable shunting system of example 31 wherein the first body region is a left atrium of a patient's heart and the second body region is a right atrium of the patient's heart.

33. An adjustable shunting system, comprising:
a shunting element; and
a shape memory actuator, the shape memory actuator comprising a plurality of actuation members arranged in a conical shape, wherein each individual actuation member of the plurality of actuation members includes—
a strut portion; and
a projection portion that is not in series electrically with the strut portion; and
a lumen extending through the shunting element and the shape memory actuator between a first orifice and a second orifice,
wherein the shape memory actuator is configured to adjust a geometry of the lumen, the first orifice, and/or the second orifice, and
wherein the system is configured such that any strain in the shape memory actuator is concentrated in the strut portion of the actuation members.

34. The adjustable shunting system of example 33 wherein the strut portions are slightly curved, and wherein the projection portions are straight.

35. The adjustable shunting system of example 33 or example 34 wherein the individual actuation members have a "Y" shape.

36. The adjustable shunting system of any of examples 33-35 wherein the individual actuation members are arranged side-by-side to form the conical shape.

37. The adjustable shunting system of any of examples 33-36 wherein, when actuated, the shape memory actuator is configured to bend at the strut portions.

38. The adjustable shunting system of any of examples 33-37 wherein the individual actuation members are integral with one another such that the shape memory actuator is a unitary structure.

39. An adjustable shunting system, comprising:
a first region comprising a shunting element; and
a second region coupled to the first region, the second region including a shape memory actuator having a plurality of struts proximate the shunting element and a plurality of projections extending from the plurality of struts; and
a lumen extending through the first region and the second region between a first orifice and a second orifice,
wherein the shape memory actuator is configured to adjust a geometry of the lumen, the first orifice, and/or the second orifice, and
wherein the system is configured such that (a) strain in the shape memory actuator is concentrated in the plurality of struts when the shape memory actuator is deformed relative to its preferred geometry, (b) individual struts of the plurality of struts are in electrical series, and (c) the plurality of projections are not in electrical series with the plurality of struts.

40. An adjustable shunting system, comprising:
a shape memory actuator having a first region and a second region connected to the first region; and
a lumen extending through the shape memory actuator between a first orifice and a second orifice,
wherein the shape memory actuator is configured to adjust a geometry of the lumen, the first orifice, and/or the second orifice, and wherein the system is configured such that strain in the shape memory actuator is concentrated in the first region of the shape memory actuator while the second region of the shape memory actuator remains generally unstrained when the shape memory actuator is deformed relative to its preferred geometry.

41. The adjustable shunting system of example 40 wherein the shape memory actuator at least partially defines the lumen, the first orifice, and the second orifice.

Conclusion

Embodiments of the present disclosure may include some or all of the following components: a battery, supercapacitor, or other suitable power source; a microcontroller, FPGA, ASIC, or other programmable component or system capable of storing and executing software and/or firmware that drives operation of an implant; memory such as RAM or ROM to store data and/or software/firmware associated with an implant and/or its operation; wireless communication hardware such as an antenna system configured to transmit via Bluetooth, Wi-Fi, or other protocols known in the art; energy harvesting means, for example a coil or antenna which is capable of receiving and/or reading an externally-provided signal which may be used to power the device, charge a battery, initiate a reading from a sensor, or for other purposes. Embodiments may also include one or more sensors, such as pressure sensors, impedance sensors, accelerometers, force/strain sensors, temperature sensors, flow sensors, optical sensors, cameras, microphones or other acoustic sensors, ultrasonic sensors, ECG or other cardiac rhythm sensors, SpO2 and other sensors adapted to measure tissue and/or bloodgas levels, blood volume sensors, and other sensors known to those who are skilled in the art. Embodiments may include portions that are radiopaque and/or ultrasonically reflective to facilitate image-guided implantation or image guided procedures using techniques such as fluoroscopy, ultrasonography, or other imaging methods. Embodiments of the system may include specialized delivery catheters/systems that are adapted to deliver an implant and/or carry out a procedure. Systems may include components such as guidewires, sheaths, dilators, and multiple delivery catheters. Components may be exchanged via over-the-wire, rapid exchange, combination, or other approaches.

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

Unless the context clearly requires otherwise, throughout the description and the examples, the words "comprise," "comprising," and the like are to be construed in an inclusive sense, as opposed to an exclusive or exhaustive sense; that is to say, in the sense of "including but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An adjustable shunting system, comprising:
   a shunting element; and
   a shape memory actuator having—
   a first plurality of petals each having a corresponding first curved segment, wherein the first plurality of petals are coupled to the shunting element,
   a second plurality of petals each having a corresponding second curved segment, wherein the second plurality of petals at least partially define a lumen through the system, and
   a plurality of curved regions coupling the first plurality of petals and the second plurality of petals, wherein individual curved regions of the plurality of curved regions are positioned between individual first curved segments and individual second curved segments;
   wherein the shape memory actuator is configured to adjust a geometry of the lumen by changing a curvature of the plurality of curved regions to move the second plurality of petals relative to the first plurality of petals, and
   wherein the system is configured such that strain in the shape memory actuator is concentrated in the plurality of curved regions when the shape memory actuator is deformed relative to its preferred geometry.

2. The adjustable shunting system of claim 1 wherein the shape memory actuator is configured such that, when an electrical current is applied to the shape memory actuator, the plurality of curved regions experiences higher resistive heating than the first plurality of petals and the second plurality of petals.

3. The adjustable shunting system of claim 1 wherein the plurality of curved regions have an axial cross-sectional area smaller than an axial cross-sectional area of the second plurality of petals.

4. The adjustable shunting system of claim 1 wherein, when electrical current flows through the shape memory actuator, the plurality of curved regions have a higher electrical current density than the second plurality of petals.

5. The adjustable shunting system of claim 1 wherein the plurality of curved regions form an annular structure, and wherein the second plurality of petals extend from the annular structure to form a conical structure.

6. The adjustable shunting system of claim 1 wherein the second plurality of petals are substantially unstrained when the actuator is deformed relative to its preferred geometry.

7. The adjustable shunting system of claim 1 wherein the first plurality of petals, the second plurality of petals, and the plurality of curved regions, comprise a unitary structure.

8. The adjustable shunting system of claim 1 wherein the system is configured such that, when the system is implanted in a patient:
the shunting element engages patient tissue and extends between a first body region and a second body region;
the shape memory actuator extends into the first body region or the second body region.

9. The adjustable shunting system of claim 1 wherein the shape memory actuator is configured such that respective curvatures of the first curved segments and the second curved segments remain generally unchanged when the curvature of the plurality of curved regions changes.

10. The adjustable shunting system of claim 1 wherein the shape memory actuator is composed of a contiguous structure that alternates between individual first petals and individual second petals, with individual curved regions between each individual first petal and individual second petal.

11. An adjustable shunting system, comprising:
a shunting element; and
a shape memory actuator, the shape memory actuator comprising a plurality of actuation members arranged in a conical shape, wherein each individual actuation member of the plurality of actuation members includes—
a curved portion; and
a projection portion extending from the curved portion, wherein individual projection portions of different actuation members are not directly in series electrically with each other; and
a lumen extending through the shunting element and the shape memory actuator between a first orifice and a second orifice,
wherein the shape memory actuator is configured to adjust a geometry of the lumen, the first orifice, and/or the second orifice, and
wherein the system is configured such that any strain in the shape memory actuator is concentrated in the curved portions of the actuation members.

12. The adjustable shunting system of claim 11 wherein the individual actuation members have a "Y" shape.

13. The adjustable shunting system of claim 11 wherein the individual actuation members are arranged side-by-side to form the conical shape.

14. The adjustable shunting system of claim 11 wherein, when actuated, the shape memory actuator is configured to bend at the curved portions.

15. The adjustable shunting system of claim 11 wherein the individual actuation members are integral with one another such that the shape memory actuator is a unitary structure.

16. An adjustable shunting system, comprising:
a shunting element; and
a shape memory actuator having a first plurality of petals coupled to the shunting element, a second plurality of petals at least partially defining a lumen through the system, and a plurality of curved regions coupling the first plurality of petals and the second plurality of petals;
wherein the shape memory actuator is configured to adjust a geometry of the lumen, and
wherein the system is configured such that (a) strain in the shape memory actuator is concentrated in the plurality of curved regions when the shape memory actuator is deformed relative to its preferred geometry, and (b) individual curved regions of the plurality of curved regions are in electrical series.

17. The adjustable shunting system of claim 16 wherein the shape memory actuator is configured such that, when an electrical current is applied to the shape memory actuator, the plurality of curved regions experiences higher resistive heating than the first plurality of petals and the second plurality of petals.

18. The adjustable shunting system of claim 16 wherein the shape memory actuator further comprises a plurality of electrical bridges extending between and electrically coupling the plurality of curved regions.

* * * * *